(12) United States Patent
Walter et al.

(10) Patent No.: US 11,213,336 B2
(45) Date of Patent: Jan. 4, 2022

(54) ALIGNMENT APPARATUS FOR USE IN HIP ARTHROPLASTY

(71) Applicant: NAVBIT HOLDINGS PTY LTD, St. Leonards (AU)

(72) Inventors: William Lindsay Walter, Wollstonecraft (AU); Shane McCarthy Donohoo, Castle Hill (AU)

(73) Assignee: NAVBIT HOLDINGS PTY LTD

( * ) Notice: Subject to any disclaimer, the term of this patent is extended or adjusted under 35 U.S.C. 154(b) by 326 days.

(21) Appl. No.: 16/522,984

(22) Filed: Jul. 26, 2019

(65) Prior Publication Data
US 2019/0357958 A1 Nov. 28, 2019

Related U.S. Application Data

(63) Continuation of application No. 15/029,238, filed as application No. PCT/AU2014/050285 on Oct. 14, 2014, now Pat. No. 10,463,415.

(30) Foreign Application Priority Data

Oct. 14, 2013 (AU) .................................. 2013903947
Jan. 17, 2014 (AU) ................................. 2014900142

(51) Int. Cl.
*A61B 17/58* (2006.01)
*A61B 17/60* (2006.01)
(Continued)

(52) U.S. Cl.
CPC ............ *A61B 17/92* (2013.01); *A61B 17/885* (2013.01); *A61B 17/8866* (2013.01);
(Continued)

(58) Field of Classification Search
CPC combination set(s) only.
See application file for complete search history.

(56) References Cited

U.S. PATENT DOCUMENTS

| 6,370,418 B1 | 4/2002 | Bernoski |
| 7,484,305 B2 | 2/2009 | Sherry et al. |
| (Continued) | | |

FOREIGN PATENT DOCUMENTS

| AU | 2009273863 B2 | 1/2010 |
| AU | 2009295253 B2 | 3/2010 |
| (Continued) | | |

OTHER PUBLICATIONS

International Search Report and Written Opinion for Application No. PCT/AU2014/050285, dated Dec. 16, 2014, 14 pages.
(Continued)

*Primary Examiner* — Sameh R Boles

(57) ABSTRACT

Hip arthroplasty apparatus and methods are described to determine an orientation of an acetabular cup impactor, the acetabular cup impactor being moveable to a desired orientation relative to a patient's pelvic region for implantation of an acetabular cup. In one embodiment an electronic orientation sensor is transitionable between a first location on the patient's pelvic region and a second location on the acetabular cup impactor. At the first location, the orientation sensor is adapted to record a reference orientation of the patient's pelvic region. At the second location the orientation sensor is adapted to determine an orientation of the acetabular cup impactor relative to the reference orientation.

11 Claims, 14 Drawing Sheets

(51) Int. Cl.
*A61F 2/00* (2006.01)
*A61B 17/92* (2006.01)
*A61F 2/46* (2006.01)
*A61B 34/20* (2016.01)
*A61B 90/00* (2016.01)
*A61B 17/88* (2006.01)
*A61B 34/00* (2016.01)

(52) U.S. Cl.
CPC ............ *A61B 34/20* (2016.02); *A61B 90/361* (2016.02); *A61F 2/4609* (2013.01); *A61F 2/4657* (2013.01); *A61B 34/25* (2016.02); *A61B 2034/2048* (2016.02); *A61B 2034/2051* (2016.02); *A61F 2002/4668* (2013.01); *A61F 2002/4687* (2013.01)

(56) References Cited

U.S. PATENT DOCUMENTS

| | | |
|---|---|---|
| 10,206,714 B2 | 2/2019 | van der Walt et al. |
| 10,271,963 B2 | 4/2019 | Lye |
| 10,603,115 B2 | 3/2020 | van der Walt et al. |
| 2010/0076505 A1* | 3/2010 | Borja .................. A61B 5/1079 606/86 R |
| 2011/0098712 A1 | 4/2011 | Sherry et al. |
| 2012/0157887 A1 | 6/2012 | Fanson et al. |
| 2012/0209117 A1 | 8/2012 | Mozes et al. |
| 2013/0053856 A1 | 2/2013 | Pennenberg |

FOREIGN PATENT DOCUMENTS

| | | |
|---|---|---|
| AU | 2011341678 B2 | 6/2012 |
| AU | 2013303055 B2 | 2/2014 |
| AU | 2015201383 A1 | 4/2015 |
| AU | 2016219992 B2 | 8/2016 |
| AU | 2018208638 A1 | 8/2018 |
| WO | 2010030809 A1 | 3/2010 |
| WO | 2012024271 A2 | 2/2012 |
| WO | 2012084739 A1 | 6/2012 |
| WO | 2014000053 A1 | 1/2014 |
| WO | 2018169980 A1 | 9/2018 |
| WO | 2018169995 A1 | 9/2018 |

OTHER PUBLICATIONS

Simon et al. "Development and Validation of a Navgational Guidance System for Acetabular Implant Placement," CVRMed-MRCAS'97, vol. 1205, Lecture Notes in Computer Science, pp. 583-592 (Springer Berlin Heidelberg 1997).

Australian Patent Examination Report for Application No. 2014336974, dated Dec. 1, 2015, 3 pages.

Australian Examination Request Acknowledgment for Application No. 2014336974, dated Nov. 26, 2015, 15 pages.

Extended European Search Report from European Patent Application No. 14853235.1, dated Dec. 15, 2017, 8 pages.

* cited by examiner

ALIGNMENT APPARATUS FOR USE IN HIP ARTHROPLASTY

CROSS-REFERENCE TO RELATED APPLICATIONS

The present application claims priority from Australian Provisional Patent Application No. 2013903947 filed on 14 Oct. 2013 and from Australian Provisional Patent Application No. 2014900142 filed on 17 Jan. 2014, the contents of which are incorporated herein by reference.

TECHNICAL FIELD

The present disclosure relates to alignment apparatus for use in hip arthroplasty.

BACKGROUND

Hip arthroplasty includes surgical procedures in which the hip joint is replaced by a prosthetic implant. The prosthetic implant can consist of different parts, including an acetabular cup designed to locate in the acetabulum (hip socket). The acetabular cup is located in position using an acetabular cup impactor, which generally takes the form of an elongate rod, having the cup at one end, and which is used to insert and orient the cup in the acetabulum. To ensure that an acetabular cup functions correctly, and does not wear significantly or cause damage to a patient, it is important that the cup is oriented and positioned correctly in the acetabulum.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Various aspects of the present disclosure provide apparatus, and methods, for use in hip arthroplasty, where an acetabular cup impactor is used to implant an acetabular cup at the acetabulum of a patient's pelvic region. A device can be mounted on the acetabular cup impactor and/or the patient's pelvic region and adapted to sense relative angular displacement of the impactor and pelvic region in order to assist with guidance of the acetabular cup impactor to a desired orientation.

According to one aspect, the present disclosure provides hip arthroplasty apparatus comprising:

an acetabular cup impactor moveable to a desired orientation relative to a patient's pelvic region for implantation of an acetabular cup; and an electronic orientation sensor transitionable between a first location on the patient's pelvic region and a second location on the acetabular cup impactor;

wherein, at the first location, the orientation sensor is adapted to record a reference orientation of the patient's pelvic region, and at the second location the orientation sensor is adapted to determine an orientation of the acetabular cup impactor relative to the reference orientation.

According to another aspect, the present disclosure provides a method of positioning an acetabular cup impactor, comprising:

locating an electronic orientation sensor at a first location on a patient's pelvic region, using the electronic orientation sensor located at the first location to record a reference orientation of the patient's pelvic region, transitioning the electronic orientation sensor from the first location to a second location on an acetabular cup impactor, the acetabular cup impactor being moveable to a desired orientation relative to the patient's pelvic region for implantation of an acetabular cup, and using the orientation sensor located at the second location to determine an orientation of the acetabular cup impactor relative to the reference orientation.

According to yet another aspect, the present disclosure provides an electronic orientation sensor, the sensor being transitionable from a first location on a patient's pelvic region to a second location on an acetabular cup impactor, the acetabular cup impactor moveable to a desired orientation relative to a patient's pelvic region for implantation of an acetabular cup, wherein, at the first location, the orientation sensor is adapted to record a reference orientation of the patient's pelvic region, and at the second location the orientation sensor is adapted to determine an orientation of the acetabular cup impactor relative to the reference orientation.

According to another aspect, the present disclosure provides a method of determining an orientation of an acetabular cup impactor, comprising:

recording a reference orientation of a patient's pelvic region using an electronic orientation sensor located at a first location on the patient's pelvic region, and determining an orientation of an acetabular cup impactor relative to the reference orientation, using the electronic orientation sensor, when the electronic orientation sensor is located at a second location on the acetabular cup impactor after being transitioned to the second location from the first location, the acetabular cup impactor being moveable to a desired orientation relative to the patient's pelvic region for implantation of an acetabular cup.

According to yet another aspect, the present disclosure provides software that, when installed on a computing device, causes the computing device to perform the method of the immediately preceding aspect.

In one embodiment, the orientation sensor is mounted or adapted to be mounted on the acetabular cup impactor, e.g. at a distal end of a handle of the impactor, via releasable fixation means. The apparatus may comprise a mount that is configured to engage both the orientation sensor and the impactor and releasably fix the positions of the orientation sensor and the impactor relative to each other. The mount may include two clamp portions, for example, adapted to clamp to the orientation sensor and the impactor, respectively. Similarly, the orientation sensor may be mounted or adapted to be mounted on the pelvic region via releasable fixation means. The apparatus may comprise a mount that is configured to engage both the orientation sensor and the pelvic region and releasably fix the positions of the orientation sensor and the pelvic region relative to each other. The mount may include two clamp portions, for example, adapted to clamp to the orientation sensor and the pelvic region, respectively. Generally, when located at the first or second location, on the pelvic region and impactor, respectively, the orientation sensor may or may not directly contact the pelvic region or impactor. However, the orientation of the orientation sensor may be substantially fixed relative to the pelvic region or impactor.

The orientation sensor may be adapted to determine the orientation of the acetabular cup impactor relative to the reference orientation in three-dimensional space. The relative orientation of the longitudinal axis of the handle and shaft of the acetabular cup impactor may be determined. Relative orientation may be determined as a degree of relative rotation about three orthogonal axes of a coordinate system (e.g. as Euler angles or otherwise). The reference orientation may provide for a local coordinate system.

The orientation sensor may determine changes in orientation based on gravitational fields, magnetic fields, and/or acceleration, for example. The orientation sensor may calculate the orientation of the impactor with respect to the specified reference orientation through monitoring of degrees of rotation about multiple axes as it transitions from the first location on the pelvic region to the second location on the impactor and as it moves during any subsequent movement of the impactor. The orientation sensor may comprise one or more of a gyroscope, a magnetic field sensor, an accelerometer, angular position sensor, and/or rotary sensor and/or one or more other types of movement or absolute or relative position sensors.

The apparatus and/or orientation sensor may comprise an output device adapted to provide information about the relative orientation of the impactor and/or the reference orientation to a clinician or other user, e.g. via text, graphics, audio and/or tactile feedback. The output device may comprise a display, speaker and/or vibrator, for example.

The apparatus and/or orientation sensor may comprise a processor adapted to determine the reference orientation and/or the relative orientation of the impactor relative to the reference orientation.

The apparatus and/or orientation sensor may comprise an input device adapted to receive an input from the clinician or other user. The input device may include one or more buttons, a keyboard, a touch sensitive screen, voice detector or otherwise. The input device may receive input from the user about a desired orientation of the impactor, e.g. desired anteversion and/or inclination angles, and/or measured orientation data, e.g. measured anteversion and/or inclination angles. The input device may receive input from the user indicative of when the orientation sensor is located on the pelvic region. The providing of an input that is indicative of when the orientation sensor is located on the pelvic region may trigger recording of the reference orientation by the orientation sensor.

The desired orientation of the impactor may correspond to an optimum implantation orientation of the acetabular cup. The optimum orientation can be defined by angles of inclination (abduction) and/or anteversion, for example. The desired orientation may be a desired angle of anteversion or a desired angle of inclination or a desired combination of anteversion and inclination angles. Anteversion and inclination angles can be defined differently, depending on whether anatomic, radiographic or operative reference frames are used. In discussions herein, desired and measured anteversion and inclination angles are defined in respect of the anatomic reference frame unless indicated otherwise. Nevertheless, the techniques described are not limited to using angles defined with respect to this reference frame only.

The desired orientation of the impactor may depend on surgical circumstances including the anatomy of the patient and preferences of the surgeon. A commonly desired anteversion angle is about 20° and a commonly desired inclination angle is about 45°. Nevertheless, the desired anteversion may be anywhere between −35° and 60°, or 0° and 40°, for example, and the desired inclination may be anywhere between 25° and 60°, or 35° and 50, for example.

In one embodiment, any one or more of the orientation sensor, the processor, the input device and the output device may be comprised in a single electronic device, such as a smartphone, tablet computer, or similar. The electronic device may run a software program or software "app" adapted to control one or more of these elements.

While an electronic orientation sensor can be used to determine orientation of an acetabular cup impactor as discussed above, an electronic orientation sensor may also be used to monitor changes in orientation in the pelvic region during surgery.

In particular, according to one aspect, the present disclosure provides hip arthroplasty apparatus comprising an electronic orientation sensor locatable on a patient's pelvic region, wherein the orientation sensor is adapted to record a reference orientation of the patient's pelvic region and subsequently monitor changes in orientation of the pelvic region relative to the reference orientation.

According to another aspect, the present disclosure provides a method of monitoring changes in orientation of a pelvic region during surgery, comprising:

locating an electronic orientation sensor on a patient's pelvic region and using the electronic orientation sensor to record a reference orientation of the patient's pelvic region, using the orientation sensor to monitor changes in orientation of the pelvic region relative to the reference orientation.

According to yet another aspect, the present disclosure provides an electronic orientation sensor, the sensor being locatable on a patient's pelvic region where it is adapted to record a reference orientation of the patient's pelvic region and monitor changes in orientation of the pelvic region relative to the reference orientation.

According to another aspect, the present disclosure provides a method of monitoring changes in orientation of a pelvic region during surgery, comprising:

recording a reference orientation of a patient's pelvic region using an electronic orientation sensor located on the patient's pelvic region, and monitoring changes in the orientation of the pelvic region relative to the reference orientation.

According to yet another aspect, the present disclosure provides software that when, installed on a computing device, causes the computing device to perform the method of the immediately preceding aspect.

The orientation sensor may be configured as described above with respect to earlier aspects. The apparatus and/or orientation sensor may comprise an output device and/or an input device as described above with respect to earlier aspects.

Monitoring of changes in the orientation of the pelvic region may be used independently of or in conjunction with determining the orientation of the acetabular cup impactor as described with respect to earlier aspects.

In general, a pelvic region can move during surgery and this can impart error into the procedure in which the orientation of the acetabular cup impactor is determined relative to a reference orientation of the pelvic region. In effect, movement of the pelvic region can cause the recorded reference orientation to be inaccurate. By monitoring changes in the orientation of the pelvic region, correction can be applied. In one embodiment, an orientation sensor is located on the pelvic region and another orientation sensor, after having recorded the reference orientation of the pelvic region, is located on the acetabular cup impactor. The orientation sensor located on the pelvic region is adapted to communicate, e.g., wirelessly or otherwise, with the orientation sensor located on the acetabular cup impactor to provide information about changes in the orientation of the pelvic region, allowing correction of a recorded reference orientation to be made. Correction may be made substantially in 'real-time'.

Various other aspects of the present disclosure also provide apparatus, and methods, for use in hip arthroplasty, in which an acetabular cup impactor is used to implant an acetabular cup at the acetabulum of a patient's pelvic region. An image capture device can be mounted on one of the acetabular cup impactor and the patient's pelvic region and adapted to capture images of the other of the acetabular cup impactor and pelvic region. The images can be presented on a display and can include one or more indicia, e.g., markers. Through observation of the one or more indicia in the images, the acetabular cup impactor can be guided to a desired orientation.

According to one aspect, the present disclosure provides hip arthroplasty, apparatus comprising:

an image capture device adapted to mount on one of an acetabular cup impactor and a patient's pelvic region, the acetabular cup impactor being moveable to a desired orientation relative to the patient's pelvic region for implantation of an acetabular cup, wherein the image capture device is adapted to capture images of the other of the acetabular cup impactor and the patient's pelvic region, including one or more first markers positioned on that other of the acetabular cup impactor and pelvic region;

a display device connected to the image capture device and adapted to display images captured from the image capture device; and a processor adapted to cause overlay of one or more second markers in the images displayed by the display device such that, when one or more of the first markers shown in the displayed images are substantially aligned with one or more of the second markers overlaid in the displayed images, the acetabular cup impactor is oriented in the desired orientation.

According to another aspect, the present disclosure provides a method of positioning an acetabular cup impactor, comprising:

mounting an image capture device on one of an acetabular cup impactor and a patient's pelvic region, the acetabular cup impactor being moveable to a desired orientation relative to the patient's pelvic region for implantation of an acetabular cup;

using the image capture device to capture images of the other of the acetabular cup impactor and the patient's pelvic region, including one or more first markers positioned on that other of the acetabular cup impactor and pelvic region;

displaying the images captured from the image capture device on a display device connected to the image capture device; and overlaying one or more second markers in the images displayed by the display device such that, when one or more of the first markers shown in the displayed images are substantially aligned with one or more of the second markers overlaid in the displayed images, the acetabular cup impactor is oriented in the desired orientation.

In one embodiment, the image capture device is mounted or adapted to be mounted on the acetabular cup impactor, and the image capture device is adapted to capture images of the patient's pelvic region, including one or more first markers positioned at the patient's pelvic region. The apparatus may comprise a mount that is configured to engage both the image capture device and the impactor and releasably fix the positions of the image capture device and the impactor relative to each other. The mount may include two clamp portions, for example, adapted to clamp to the image capture device and the impactor, respectively.

In this embodiment, the one or more first markers may comprise one or more anatomical landmarks. For example, the one or more anatomical landmarks may comprise one or both of the anterior superior iliac spines. In one embodiment, the one or more first markers comprise a vector line extending between anterior superior iliac spines. The vector line may be an imaginary line between the anterior superior iliac spines or may be a line that is drawn on the patient's pelvic region. Alternatively, the vector line may be a line that is drawn on, or provided by an edge, channel or visual feature, of a marker element, e.g. a rod, bar or other device, which is connected to or positioned adjacent the pelvis.

The apparatus may comprise a tilt sensor. The tilt sensor may be fixed in relation to the acetabular cup impactor and/or the image capture device. The tilt of the impactor and/or image capture device can be determined as the image capture device moves, e.g. as a result of moving the acetabular cup impactor. The tilt may be measured relative to a horizontal plane, for example.

The image capture device, in addition to any one or more of the display device, the processor and the tilt sensor, may be comprised in a single electronic device, such as a smartphone, tablet computer, or similar. The electronic device may run a software program or software "app" adapted to control the display device, processor and/or tilt sensor in accordance with the apparatus and methods of the present disclosure.

The mount of the apparatus may be adapted to engage both the electronic device and the impactor and releasably fix the positions of the electronic device and the impactor relative to each other. The mount may include two clamp portions, for example, adapted to clamp to the electronic device and the impactor, respectively.

The desired orientation of the impactor may correspond to an optimum implantation orientation of the acetabular cup. The optimum orientation can be defined by angles of inclination (abduction) and/or anteversion, for example. The desired orientation may be a desired angle of anteversion or a desired angle of inclination or a desired combination of anteversion and inclination angles.

The processor may be adapted to receive orientation data related to the impactor. The orientation data may include desired orientation of the impactor, e.g. desired anteversion and/or inclination angles, and/or measured orientation data, e.g. measured anteversion and/or inclination angles. Based on the received orientation data, the processor may determine appropriate positions and/or orientations for the one or more second markers displayed in the images. A commonly desired anteversion angle is about 20° and a commonly desired inclination angle is about 45°. Nevertheless, depending on circumstances including the anatomy of the patient and preferences of the surgeon, the desired anteversion may be anywhere between 0° and 40°, or even −35° and 60°, and the desired inclination may be anywhere between 35° and 50, or even 25° and 60°.

According to one aspect, the present disclosure provides a method of guiding the positioning of an acetabular cup impactor in a hip arthroplasty procedure, the method being adapted for use with hip arthroplasty apparatus that comprises:

an image capture device adapted to mount on one of an acetabular cup impactor and a patient's pelvic region, the acetabular cup impactor being moveable to a desired orientation relative to the patient's pelvic region for implantation of an acetabular cup, wherein the image capture device is adapted to capture images of the other of the acetabular cup impactor and the patient's pelvic region, including one or more first markers positioned on that other of the acetabular cup impactor and pelvic region; and a display device connected to the image capture device and adapted to display images captured from the image capture device; and a processor adapted to cause overlay of one or more second markers in the images displayed by the display device such that, when one or more of the first markers shown in the displayed images are substantially aligned with one or more of the second markers overlaid in the displayed images, the acetabular cup impactor is oriented in the desired orientation, the method comprising:

determining the position and orientation for the one or more second markers to be overlaid in the images displayed by the display device based on received orientation data including a desired angle of orientation of the acetabular cup impactor and a measured orientation angle of the acetabular cup impactor data.

In one embodiment, the received orientation data comprises a desired anteversion angle of the acetabular cup impactor and a measured inclination angle of the impactor. In another embodiment, the received orientation data comprises a desired inclination angle of the acetabular cup impactor and a measured anteversion angle of the impactor. In another embodiment, the received orientation data comprises desired anteversion and inclination angles of the acetabular cup impactor, and measured anteversion and inclination angles of the impactor.

In one embodiment, one or more of the measured angles may be obtained at least in part through a feature recognition process. For example, by determining the positioning of one or more of the first markers in the images, one or more of the angles of anteversion and inclination of the acetabular cup impactor may be measured.

Additionally or alternatively, the measured orientation angle may be obtained at least in part by the tilt sensor, particularly when the tilt sensor is fixed in position relative to the impactor. Since the tilt sensor may determine tilt with reference to a gravitational field, whether or not the tilt sensor provides a measured anteversion angle or measured inclination angle for the impactor can depend on the orientation of the patient during surgery, e.g. whether or not they are in a supine position or a lateral recumbent position.

In one embodiment, the tilt sensor may provide measurements of one of the anteversion angle and the inclination angle, which measurements can be presented and continually updated on the display (or on a different display). Following from this, the second markers may be used to guide orienting of the impactor with respect to the other one of the anteversion angle and the inclination angle only. Thus, the surgeon may orient the impactor so that it has one of the desired anteversion angle and the desired inclination angle by simply by observing changes in the displayed measurements from the tilt sensor and moving the impactor accordingly, and the surgeon may orient the impactor so that it has the other of the desired anteversion angle and the desired inclination angle by aligning one or more of the first markers shown in the displayed images with one or more of the second markers overlaid in the displayed images.

The step of determining the positions and/or orientations for the one or more second markers may be carried out by the processor.

In one aspect, the present disclosure provides software that causes the processor to perform the method of the preceding aspect. The software may cause the processor to perform the method of the preceding aspect when installed on an electronic device comprising the processor.

As indicated, the processor may be comprised in an electronic device such as a smartphone, tablet computer, laptop computer, personal computer or otherwise. The electronic device may comprise other features of the apparatus described above, such as the image capture device, display device and/or tilt sensor. The software may take the form of application software (e.g. an "app"), which may be downloadable from a media library such as iTunes™ or Android™ media libraries or otherwise.

Nonetheless, more generally, it will be recognised that processers or processing apparatus as disclosed herein may comprise a number of control or processing modules for controlling one or more components of the apparatus and may also include one or more storage elements, for storing desired angle data, measured angle data, orientation data, and/or patient data, etc. The modules and storage elements can be implemented using one or more processing devices and one or more data storage units, which modules and/or storage devices may be at one location or distributed across multiple locations and interconnected by one or more communication links. Processing devices may include tablets, smartphones, laptop computers, person computers personal digital assistants and other types of electronic devices, including systems manufactured specifically for the purpose of carrying out methods according to the present disclosure.

Further, the processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g. RAM) and/or non-volatile (e.g. ROM, disk) memory or otherwise.

The processor may be adapted to adjust the orientation of the one or more second markers that are overlaid in the images displayed by the display device depending on the received orientation data. For example, the processor may be adapted to continually adjust the orientation of the one or more second markers that are overlaid in the images displayed by the display device depending on measured orientation data. The one or more second markers may comprise lines and the orientation of the lines (the angle that the lines extend across all or part of the displayed images) may be adjusted. In alternative embodiments, the one or more second markers may comprise dots, shapes, graduated shading and/or colouring, etc.

The orientation of one or more second markers that are overlaid in the images displayed by the display device may be at least partially dependent on the position in the images at which they are overlaid. For example, if one of the second markers is to be overlaid towards a lower region of the image, the lower region corresponding to a part of the image generated with respect to a lower portion or angle of the image capture device's field of view, the processor can be configured to orientate that second marker differently to an orientation that it would be overlay one of the second markers towards a higher region of the image, the higher region corresponding to a part of the image generated with respect to a higher portion or angle of the image capture device's field of view. The processor may be adapted to continually determine, for different positions of the image (e.g. at different distances from a central, 0°, axis of the image capture device's field of view), an appropriate orientation for a second marker that is to be overlaid at that position, depending on the desired and measured anteversion and/or inclination angles. Generally, this approach recognises that the field of view of the image capture device will necessarily cover a range of angles and therefore the orientation of items as seen within images captured by the image capture device, relative to the impactor on which image capture device is mounted, will partially depend on where in the field of view of the camera those items are positioned. The processor may be adapted to determine a plurality of different second marker orientation angles for multiple positions in the images at which second markers are to be overlaid, and the processor may be adapted to overlay the plurality of second markers in the images accordingly.

In one embodiment, the patient is in a supine position. The image capture device and the tilt sensor are mounted on the impactor. The tilt sensor is adapted to measure anteversion angles of the impactor and continually provide the measured anteversion angles to the processor. The processor is also adapted to receive a data input, or is pre-programmed, with the desired inclination angle of the impactor. Based in part on the continually measured anteversion angles and the desired inclination angle, the processor is adapted to continually determine an appropriate orientation of each one of a plurality of the second markers that are to be overlaid over the images, for different positions in the images (e.g. for different distances in the image from the central axis of the image capture device's field of view), and the processor is adapted to overlay the second markers in the images accordingly. Since the appropriate orientation for the second markers will change depending on the tilt of the impactor (the measured anteversion), the orientation of the second markers in the images may change substantially in 'real time' as the surgeon moves the impactor. Meanwhile, the processor is adapted to present the measured anteversion angle on the display and continually update the display as the measured anteversion angle changes.

In this embodiment, when at least one first marker visible in the image is brought substantially in alignment with its nearest second marker or second markers, the impactor will be oriented with substantially the desired inclination angle. At the same time, the desired anteversion angle can be achieved by observing the measured anteversion angle presented on the display, and moving of the impactor accordingly.

In an alternative embodiment, the patient is in a lateral recumbent position. The image capture device and the tilt sensor are mounted on/fixed to the impactor. Thus, the tilt sensor, in contrast to the preceding embodiment, is adapted to measure inclination angles of the impactor and continually provide measured inclination angles to the processor. The processor is also adapted to receive a data input, or is pre-programmed, with the desired anteversion angle of the impactor. Based in part on the continually measured inclination angles and the desired anteversion angle, the processor is adapted to continually determine an appropriate orientation of each one of a plurality of the second markers that are to be overlaid over the images, for different positions in the images (e.g. for different distances in the image from the central axis of the image capture device's field of view), and the processor is adapted to overlay the second markers in the images accordingly. Since the appropriate orientation for the second markers will change depending on the tilt of the impactor (the measured inclination), the orientation of the second markers in the images may change substantially in 'real time' as the surgeon moves the impactor. Meanwhile, the processor is adapted to present the measured inclination angle on the display and continually update the display as the measured inclination angle changes.

In this embodiment, when at least one first marker visible in the image is brought substantially in alignment with its nearest second marker or second markers, the impactor will be oriented with substantially the desired anteversion angle. At the same time, the desired inclination angle can be achieved by observing the measured inclination angle presented on the display, and moving of the impactor accordingly.

In an alternative embodiment, the image capture device is mounted or adapted to be mounted on the pelvic region, e.g. on the pelvic bone, and the image capture device is adapted to capture images of the acetabular cup impactor, including one or more first markers positioned on the acetabular cup impactor. The apparatus may comprise a mount that is configured to engage both the image capture device and the pelvic region and releasably fix the positions of the image capture device and the pelvic region. The mount may include two clamp portions, adapted to clamp to the image capture device and the pelvic region, respectively.

In this embodiment, the one or more first markers may comprise one or more features of the acetabular cup impactor and/or one or more navigation elements attached to the acetabular cup impactor. For example, the impactor may be generally elongate and may define a longitudinal axis and the one or more first markers comprise a vector line extending along the longitudinal axis. The vector line may be an imaginary line, a line that is drawn on the impactor, or a line provided by an edge, channel or other visual feature of the impactor. Additionally or alternatively, other types of markers may be used. For example, one or more circles, part-circles, ellipses, part-ellipses, spheres or other shapes may be provided in fixed positions relative to the impactor. Where a plurality of first markers is provided, the markers may be positioned at different distances along the longitudinal axis of the impactor, for example.

This embodiment may differ from one or more of the embodiments described previously in that it may not make use of a tilt sensor to continually determine one of the anteversion and inclination angles. Particularly when the image capture device and the tilt sensor are integrated into a single device, since the image capture device is mounted to the pelvic region, which remains substantially stationary relative to the gravitational field when the impactor is moved, a tilt sensor may be not be available for monitoring changes in anteversion or inclination of the impactor. Nonetheless, the tilt sensor may be used to determine the orientation of the pelvis, before, during and/or after surgery, as an alignment tool.

A calibration procedure may be employed in order to determine an appropriate position for one or second markers to be overlaid on the displayed images, such that when one or more of the first markers shown in the displayed images are substantially aligned with one or more of the second markers overlaid in the displayed images, the acetabular cup impactor is oriented in the desired orientation. The calibration procedure may be carried out to determine, generally, the pivot point of the impactor relative to the image capture device, the length of the impactor and/or the positions of the one or more markers on the impactor. Based on these details, the processor may determine where the one or more second markers should be overlaid in the images to guide positioning of the impactor to the desired orientation.

The calibration procedure may be performed with the impactor and acetabular cup engaged in the hip socket of the pelvic region and/or performed remotely from the pelvic region.

During the calibration procedure, the processor may overlay one or more third markers on the images, which third markers indicate one or more positions at which one or more of the first markers should be located during the calibration procedure. When positioned accordingly, a user action may be required to provide further information to the processor. For example, when one of the first markers is aligned with one of the third markers, a user may be required to identify on the display the location of a different one of the first markers and/or the location of the shaft of the impactor. The identification may be performed by touching the display (if a touch screen display is used) or moving and 'clicking' a visible cursor in the image. This process of alignment with a third marker and subsequent location identification may be repeated multiple times (e.g. 2, 3, 4 or more times), but with the one or more third markers positioned differently in the images in each instance.

In some embodiments, second markers may not be overlaid over the images and other types of indicia may be used. Indicia representing both the anteversion and inclination angles of the impactor may be displaced substantially in 'real time' on the display, for example, enabling a surgeon to move the impactor to the desired orientation based on observation of changes to the displayed angles.

Following from this, according to a one aspect, the present disclosure provides hip arthroplasty, apparatus comprising:

an image capture device adapted to mount on one of an acetabular cup impactor and a patient's pelvic region, the acetabular cup impactor being moveable to a desired orientation relative to the patient's pelvic region for implantation of an acetabular cup, wherein the image capture device is adapted to capture images of the other of the acetabular cup impactor and the patient's pelvic region, including one or more first markers positioned on that other of the acetabular cup impactor and pelvic region;

a display device connected to the image capture device and adapted to display images captured from the image capture device; and a processor adapted to provide one or more indicia in the images displayed by the display device to guide the acetabular cup impactor to the desired orientation.

According to another aspect, the present disclosure provides a method of positioning an acetabular cup impactor, comprising:

mounting an image capture device on one of an acetabular cup impactor and a patient's pelvic region, the acetabular cup impactor being moveable to a desired orientation relative to the patient's pelvic region for implantation of an acetabular cup;

using the image capture device to capture images of the other of the acetabular cup impactor and the patient's pelvic region, including one or more first markers positioned on that other of the acetabular cup impactor and pelvic region;

displaying the images captured from the image capture device on a display device connected to the image capture device; and providing one or more indicia in the images displayed by the display device to guide the acetabular cup impactor to the desired orientation.

According to yet another aspect, the present disclosure provides a method of guiding the positioning of an acetabular cup impactor in a hip arthroplasty procedure, the method being adapted for use with hip arthroplasty apparatus that comprises:

an image capture device adapted to mount on one of an acetabular cup impactor and a patient's pelvic region, the acetabular cup impactor being moveable to a desired orientation relative to the patient's pelvic region for implantation of an acetabular cup, wherein the image capture device is adapted to capture images of the other of the acetabular cup impactor and the patient's pelvic region, including one or more first markers positioned on that other of the acetabular cup impactor and pelvic region; and a display device connected to the image capture device and adapted to display images captured from the image capture device; and a processor adapted to provide one or more indicia in the images displayed by the display device to guide the acetabular cup impactor to the desired orientation, the method comprising:

determining an orientation of the acetabular cup impactor data based at least on a positioning of the one or more first markers in the images; and based on the determined orientation, providing one or more indicia in the images displayed by the display device to guide the acetabular cup impactor to the desired orientation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments are now described with reference to the accompanying drawings, in which.

DESCRIPTION OF EMBODIMENTS

Figure 1:
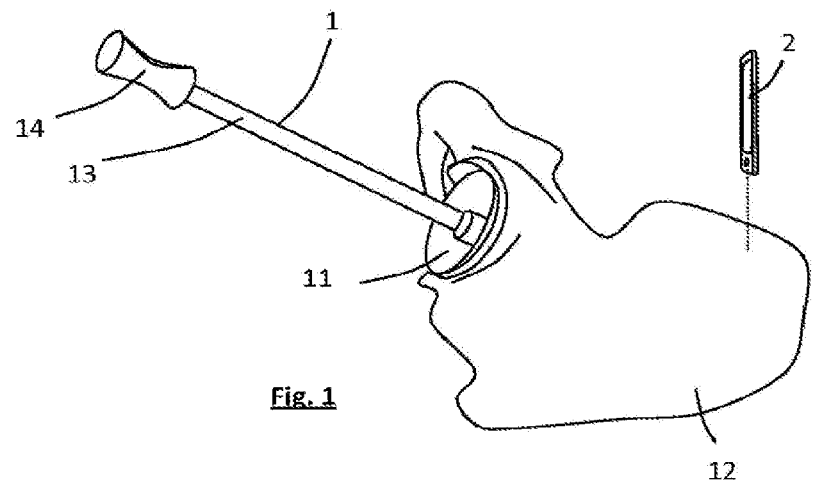
FIG. 1 shows apparatus according to an embodiment of the present disclosure with an electronic device at a first location.
Figure 2:
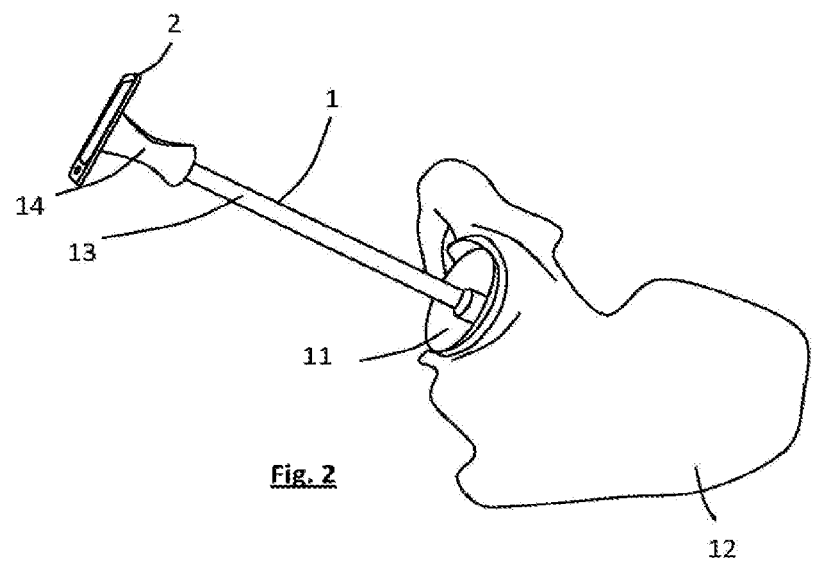
FIG. 2 shows the apparatus of FIG. 1 with the electronic device at a second location.

FIGS. 1 and 2 show apparatus according to an embodiment of the present disclosure. The apparatus includes an acetabular cup impactor 1, adapted to drive and implant an acetabular cup 11 into position at the acetabulum of a patient's pelvic bone 12, and an electronic device 2, the electronic device 2 being adapted to be located at a first location on the pelvic region (see FIG. 1) and subsequently located at a second location on the acetabular cup impactor 1 (see FIG. 2).

Figure 3:
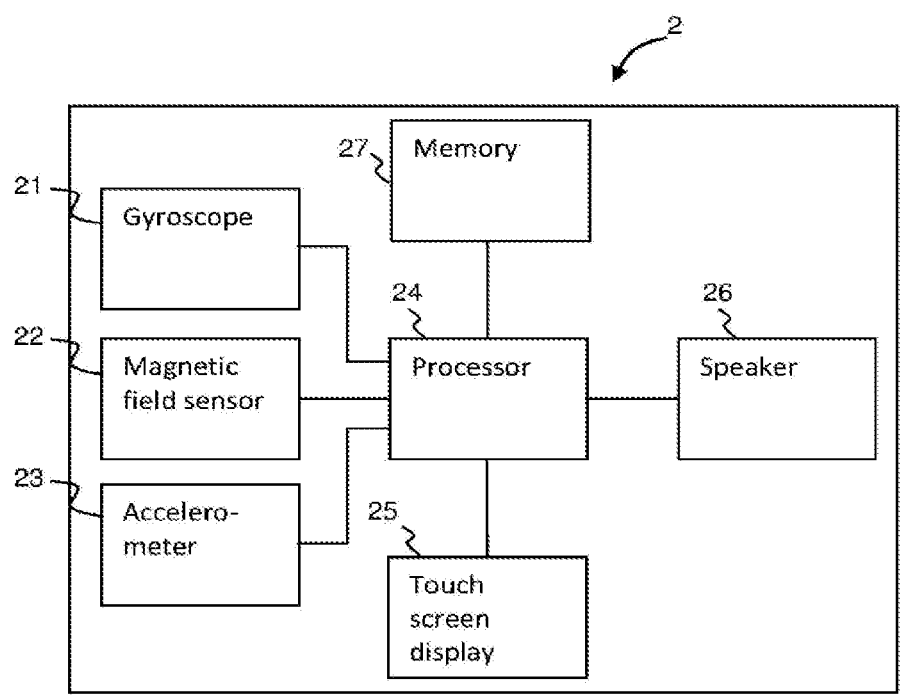
FIG. 3 shows a schematic view of elements of the electronic device of FIG. 1.

With reference also to FIG. 3, the electronic device 2 acts at least in part as an orientation sensor through inclusion of a gyroscope 21, a magnetic field sensor 22 and an accelerometer 23 connected to a processor 24. In alternative embodiments, one or more of these sensors may be excluded. For example, the accelerometer 23 may be excluded or otherwise. The electronic device 2 further includes an input device connected to the processor 24 that is in the form of a touch screen display 25, which touch screen display 25 also provides an output device in conjunction with a speaker 26. A memory 27 is provided for data storage and retrieval. In this embodiment, the electronic device 2 is a Smartphone, e.g. an iPhone™, although a variety of different electronic devices may be used. Further, the sensors, processor, input and output devices need not be integrated into a single device. For example, in one embodiment, the display and speaker may be maintained at a location that is remote from the pelvic region and impactor, and may communicate with the processor 24 via wires or wirelessly.

The acetabular cup impactor 1 includes a shaft 13 extending distally from the acetabular cup/pelvic region, and a handle 14 at the distal end of the shaft. In this embodiment, when at the second location as shown in FIG. 2, the electronic device 2 is releasably fixed to the distal end of the handle 14 such that planar face of the electronic device, which includes the display 25, is fixed at an orientation that is substantially orthogonal to the impactor shaft 13. A mount (not shown) is adapted to clamp the electronic device 2 to the handle 14. The electronic device 2 may be encased in a plastic covering. The plastic covering may hermetically seal the electronic device 2.

The gyroscope 21, magnetic field sensor 22 and accelerometer 23 of the electronic device provide in combination with the processor 24 an orientation sensor that can track orientation of the electronic device 2, and hence the acetabular cup impactor 1 when mounted thereon. By sensing movement of the electronic device 2 within the surrounding gravitational and magnetic fields, and optionally also acceleration and deceleration of the device 2, changes in orientation about three orthogonal axes of a coordinate system can be monitored.

In use, as part of a calibration process, the electronic device 2 is mounted at the first location on the pelvic region of the body as shown in FIG. 1. In particular, in this embodiment in which the patient is in a supine position, it is mounted so that its bottom edge substantially lines up with a vector line extending between right and left anterior superior iliac spines (ASIS) of the pelvic bone 12. In alternative embodiments, the electronic device may be mounted so that its bottom edge is at a different angle to this vector line, such as a 45 degree angle. In FIG. 1 and subsequent Figures, for simplicity, the pelvic bone of the patient is represented independently of any other body parts or body tissue. In practice, other body parts and body tissue would, of course, be present.

Figure 4:
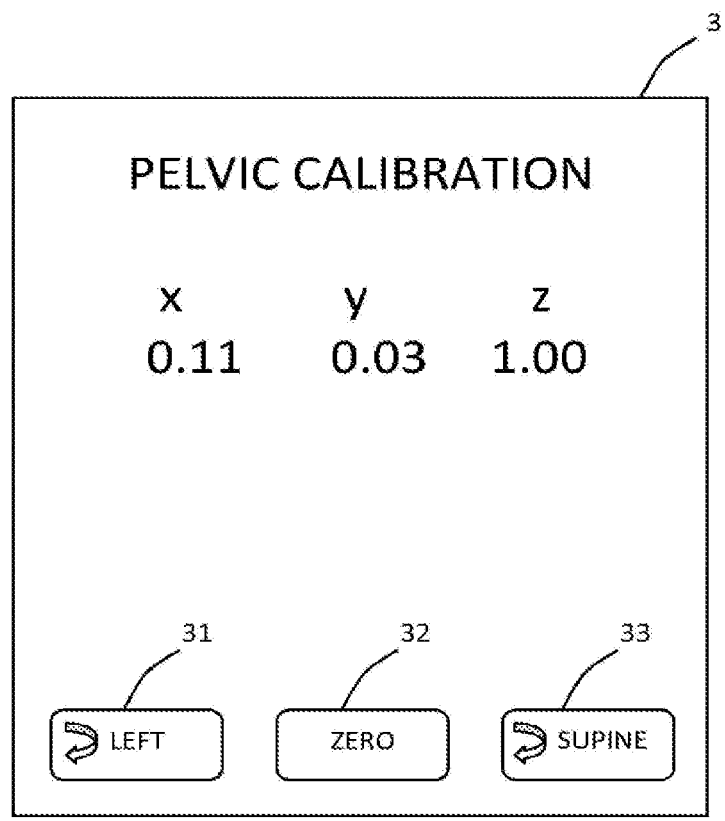
FIG. 4 shows a pelvic calibration display screen from the electronic device of FIG. 1.

When the electronic device 2 is at the first location, the display 25 is adapted to display a pelvic calibration screen 3 as represented in FIG. 4. Three touch-screen buttons are provided on the screen 3. One of the buttons 31 enables input of the hip side of the patient, in particular so that a clinician or other use can indicate if the hip replacement is being carried out in relation to the left or right hip. Another of the buttons 33 enables input of the positioning of the patient, in particular so that the clinician or other user can indicate if the patient is in a supine or a lateral orientation. Finally, a zero button 32 is provided, which is to be pressed once the positioning of the patient and hip side have been inputted, and once the electronic device 2 is securely positioned at the first location (i.e. at the appropriate calibration position). When the zero button 32 is pressed, the electronic device 2 records its orientation, and hence the orientation of the pelvic region, and uses this as a reference orientation against which all subsequent changes in orientation of the electronic device 2 are compared.

Figure 5:
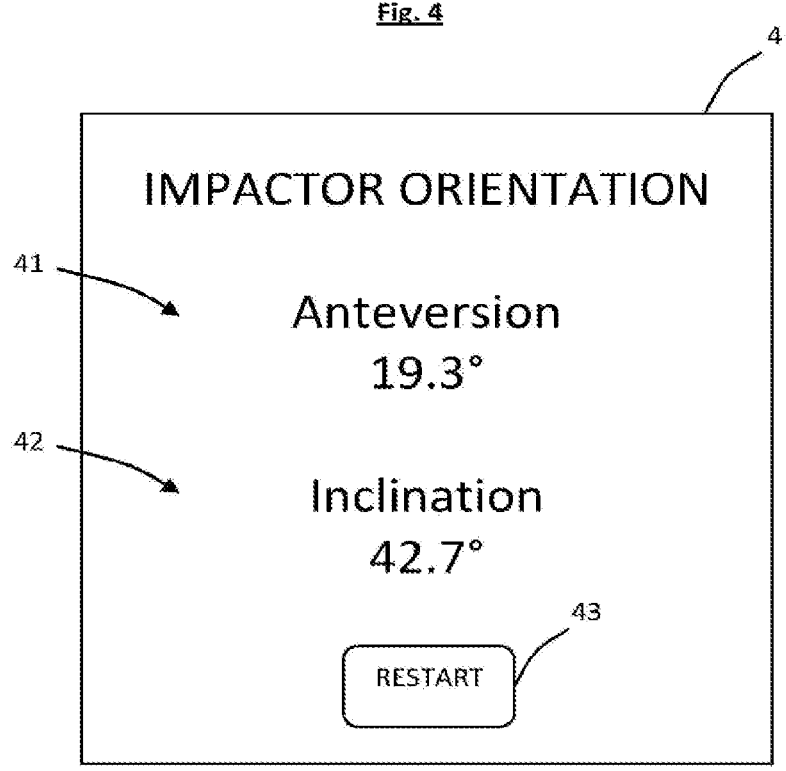
FIG. 5 shows an impactor orientation display screen from the electronic device of FIG. 1.

After calibration ('zeroing'), the electronic device 2 is transitioned from the first location on the pelvic region to the second location on the impactor 1, in particular at the distal end of the handle 14 as shown in FIG. 2, where it displays an impactor orientation screen 4 as represented in FIG. 5. As it transitions from the calibration position, the electronic device 2 continually monitors changes in its orientation relative to the reference orientation such that, when mounted on the handle 14, it immediately knows its orientation, and hence the orientation of the impactor shaft 13, relative to the reference orientation. The electronic device 2 can therefore display on the screen 4 the orientation of the impactor shaft 13 relative to the reference orientation (in terms of angle of anteversion 41 and angle of inclination 42 in this embodiment) and it can monitor and update the orientation on the screen, as it moves with the impactor 1 thereafter. Thus, the clinician or other user can observe the angles of anteversion and inclination in 'real-time' on the display, allowing him/her to move the acetabular cup impactor 1 to a desired orientation. The desired orientation may be an angle of 20° anteversion and 45° inclination or otherwise. Once completed, or if recalibration of the reference orientation is desired, a button 43 can be pressed to restart the procedure.

Example mathematics that may be employed in this or other embodiments is set forth below, where:

RI=radiographic inclination pelvic reference frame
RA=radiographic anteversion pelvic reference frame
AI=anatomic inclination pelvic reference frame
AA=anatomic anteversion pelvic reference frame
ri=radiographic inclination gravity reference frame
ra=radiographic anteversion gravity reference frame
ai=anatomic inclination gravity reference frame
aa=anatomic anteversion gravity reference frame
y'−y=yaw
r=roll
P=pelvic roll Assuming no pelvic roll:
Yaw gives radiographic inclination (RI)
Roll gives radiographic anteversion (RA)
To convert to anatomic anteversion (AA) and anatomic inclination (AI) per Murray (D. W. Murray: The definition and measurement of acetabular orientation. *J Bone Joint Surg* [*Br*] 1993; 75-B: 228-32):

$$Tan(AA)=Tan(RA)/Sin(RI)$$

$$Cos(AI)=Cos(RI)*Cos(RA)$$

Therefore:

$$Anatomic\ Anteversion=\arctan(\tan(r)/\sin(y'-y))$$

$$Anatomic\ Inclination=\arccos(\cos(y'-y)*\cos(r))$$

If there is pelvic roll 'yaw' is calculated about a vertical axis that has rolled and roll calculated against the same axis.
Supine position with pelvic roll to the right in a right hip:

$$AA-P=aa$$

$$AA=aa+P$$

$$AI=ai$$

$$ra=r$$

$$ri=y'-y$$

$$Cos(AI)=\cos(ai)$$

$$=Cos(ri)*Cos(ra)$$

$$AI=\arccos(\cos(y'-y)*\cos(r))$$

$$AA=\arctan(\tan(r)/\sin(y'-y))+P$$

And for a left hip:

$$AI=\arccos(\cos(y-y')*\cos(r))$$

$$AA=\arctan(\tan(r)/\sin(y-y'))-P.$$

Figure 6:
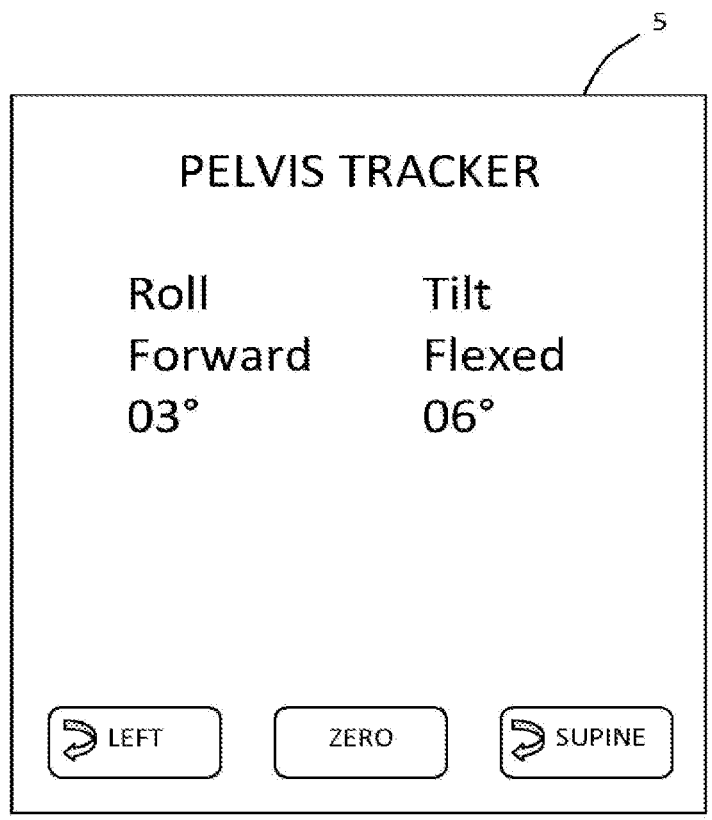
FIG. 6 shows a display screen from an electronic device used in another embodiment of the present disclosure.

In another embodiment of the present disclosure, the apparatus described above with reference to FIGS. 1 to 4 is adapted for use in tracking changes in orientation of the pelvic region during surgery. An electronic device is mounted to the pelvis, e.g. as represented in FIG. 1. However, after carrying out a calibration process as described with reference to FIG. 4, the electronic device 2 is maintained in position on the pelvic region and is used to track motion of the pelvic region in at least two rotational axes (pitch (tilt) and roll) or preferably three rotational axes (pitch, roll and yaw). The device 2 is adapted to display a pelvis tracking screen 5 as represented in FIG. 6, which presents the current orientation of the pelvis substantially in 'real-time' during the surgical procedure. The electronic device 2 is adapted to record the pelvic movement in the memory 27 throughout the surgical procedure. In one embodiment, predetermined limits on the degree of motion of the pelvis are inputted by the clinician into the electronic device 2, and an audible signal using the speaker 26 or other type of alarm is provided as a warning when these limits are exceeded.

Figure 7:
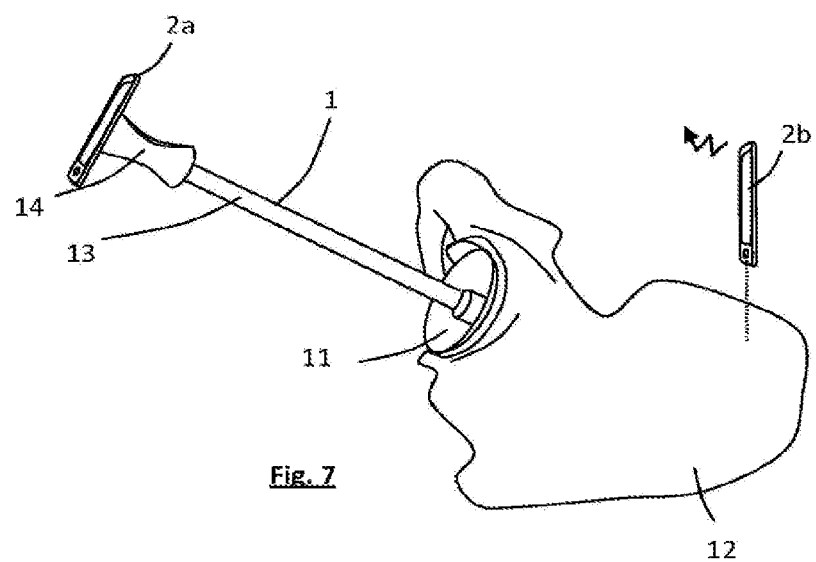
FIG. 7 shows apparatus according to another embodiment of the present disclosure.

In yet another embodiment, the approach described with respect to the two preceding embodiments is combined through the provision of two electronic devices 2a, 2b. Referring to FIG. 7, a first one of the electronic devices 2a is used as described above to record a reference orientation of the pelvic region prior to transitioning to the second location where it determines the orientation of the impactor 1 relative to the reference orientation. Further, a second one of the electronic devices 2b is used as described above to record a reference orientation of the pelvic region and is then maintained on the pelvic region to track changes in orientation of the pelvic region during surgery. The second electronic device 2b is adapted to wirelessly communicate with first electronic device 2a to provide information about changes in the orientation of the pelvic region, allowing correction of the reference orientation recorded by the first electronic device 2a to be made substantially in 'real-time'.

Figure 8:
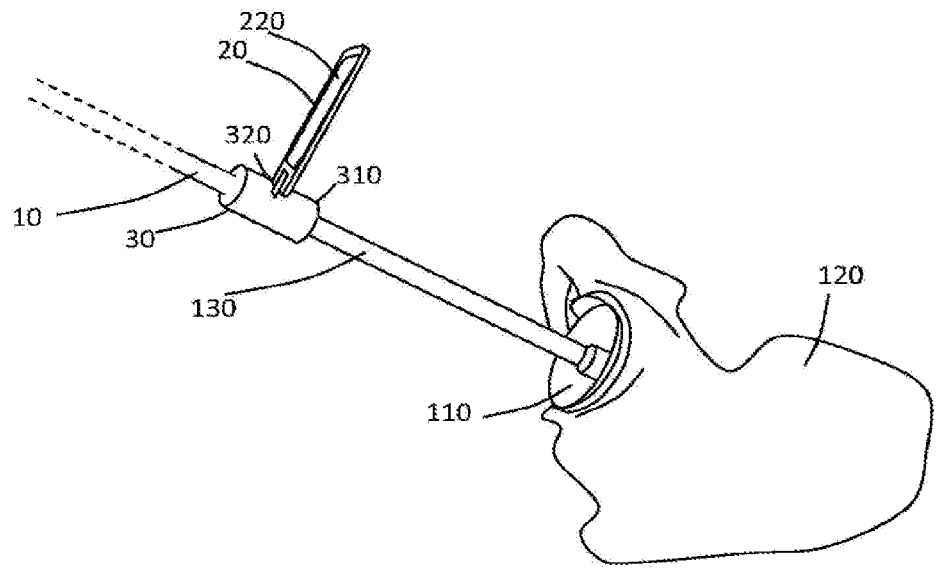
FIG. 8 shows apparatus according to another embodiment of the present disclosure.
Figure 10:
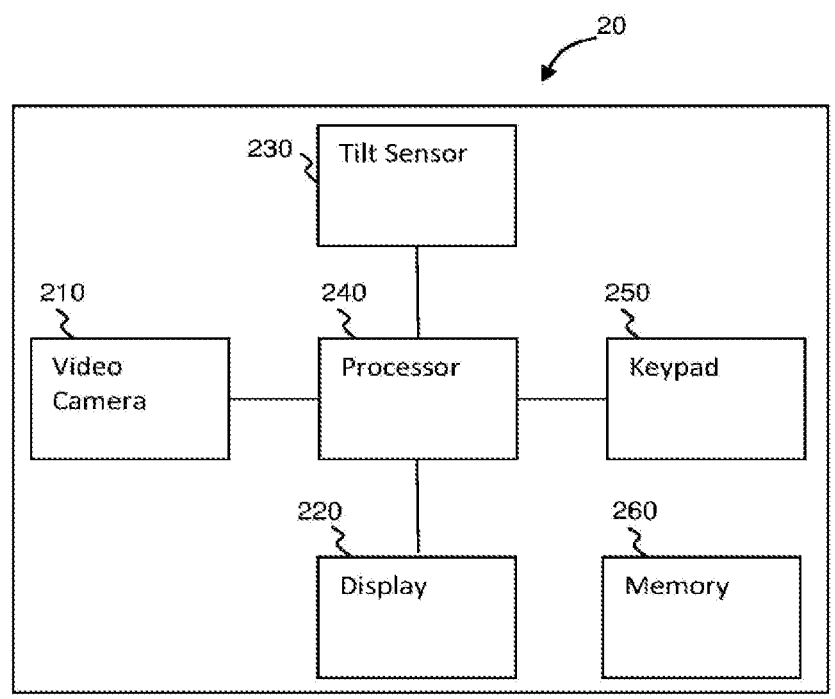
FIG. 10 shows a schematic view of elements of an electronic device used in the apparatus of FIG. 8.

FIG. 8 shows apparatus according to an embodiment of the present disclosure. The apparatus includes an acetabular cup impactor 10, adapted to drive and implant an acetabular cup 110 into position at the acetabulum of a patient's pelvic bone 120, and an electronic device 20, the electronic device 20 being mounted on the impactor 10. With reference also to FIG. 10, the electronic device 20 includes an image capture device in the form of a video camera 210, a digital display 220, a tilt sensor 230, a processor 240, a touch keypad 250 and a memory 260 for data storage and retrieval. In this embodiment, the electronic device 20 is a Smartphone, e.g. an iPhone™, although a variety of different electronic devices may be used. The camera 210, display 220, tilt sensor 230 and processor 240 need not be integrated into a single device 20, nor mounted on the impactor 10. For example, in one embodiment, the display and/or processor may be located remotely from the impactor 10.

The electronic device 20 is releasably fixed to the shaft 130 of the impactor 10 via a mount 30 such that the camera of the electronic device faces the pelvic bone 120 and, more generally, the pelvic region of the patient. The mount 30 is adapted to clamp to the shaft 130 of the impactor 10 through provision of a sleeve portion 310 that at least partially extends around the impactor shaft 130. The mount 30 is also adapted to clamp to the electronic device 20 through provision of one or more arms 320 that project from the sleeve portion 310 and abut opposing sides or edges of the electronic device 20. The electronic device 20 may be encased in a plastic covering. The plastic covering may hermetically seal the electronic device 20.

Figure 9:
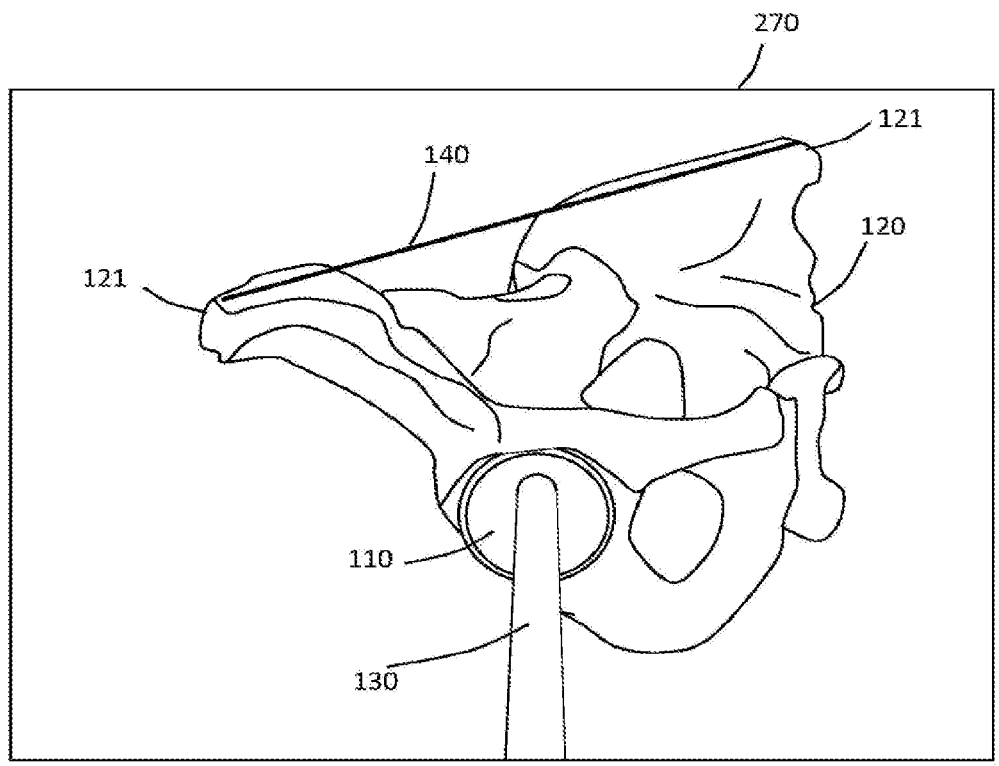
FIG. 9 shows an image of a pelvic region captured by a camera of the apparatus of FIG. 8.

The camera 210 of the electronic device 20 is adapted to sequentially capture a plurality of images of the pelvic region of the patient (i.e. video the pelvic region of the patient), and the images are presented, substantially in 'real time', on the display 220. The pelvis 120 includes a first marker 140 thereon, more particularly a vector line 140 extending between right and left anterior superior iliac spines (ASIS) 121 that is imagined or drawn on bone and/or tissue between ASIS 121. With reference to FIG. 9, which shows an example image (frame) 270 as presented on the display 220, the ASIS vector line 140 is represented in the image 270. In FIG. 8 and subsequent Figures, for simplicity, the pelvic bone 120 of the patient is represented independently of any other body parts or body tissue. In practice, other body parts and body tissue would, of course, be present.

The processor 240 of the electronic device 10 is adapted to receive orientation data related to the impactor 10 (and the acetabular cup 110). In this embodiment, the patient is located in a supine position, and the orientation data received by the processor 240 includes a desired inclination angle for the impactor and measured anteversion angles for the impactor. The desired inclination angle, which is 45° in this example, is input into the electronic device 20 using the touchscreen keypad 250. The anteversion angle is continually measured using the tilt sensor of the electronic device 20.

Figure 13:
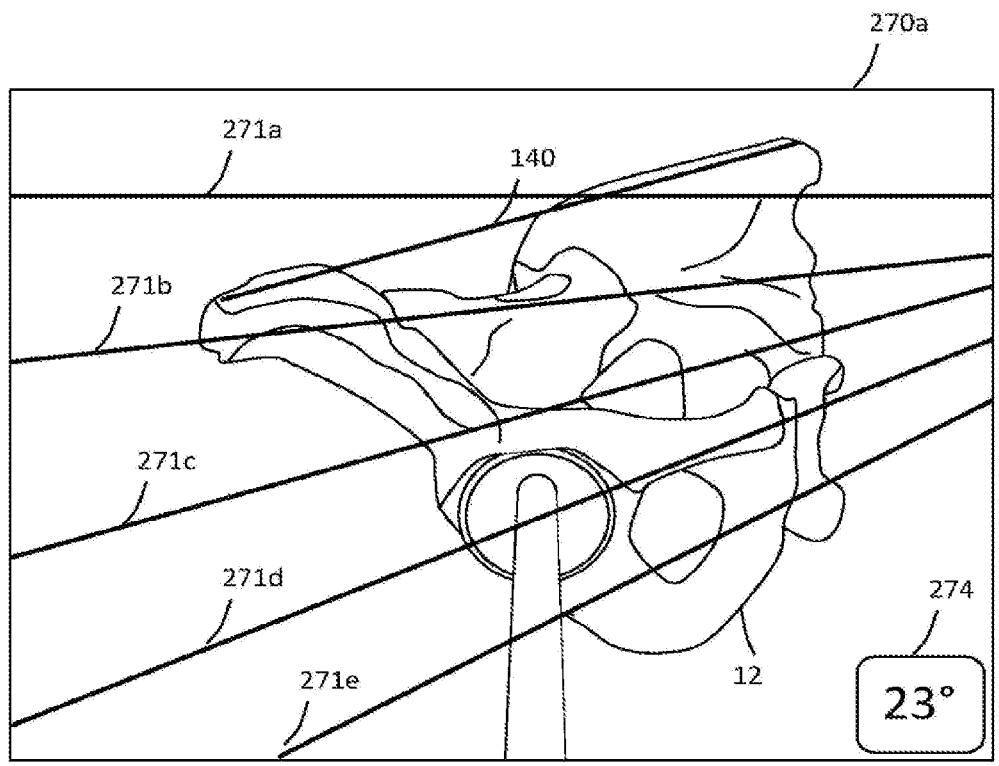
FIG. 13 shows the plurality of marker lines of FIG. 12 overlaid on the image of FIG. 9, with the acetabular cup impactor in a first position relative to the pelvic region.
Figure 14:
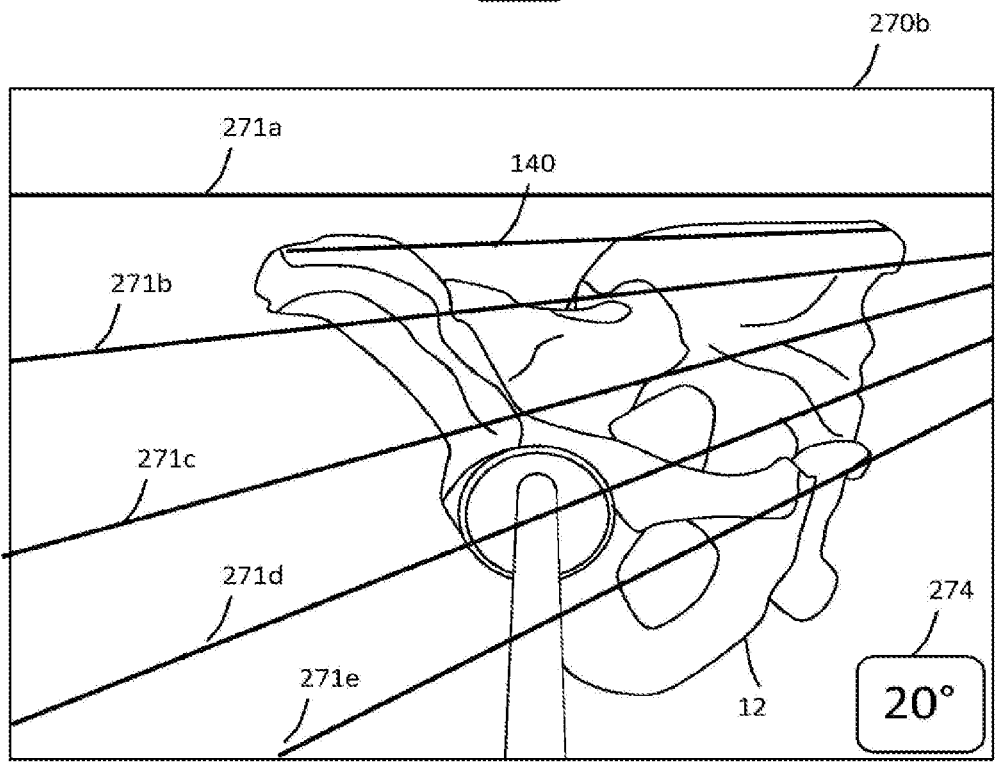
FIG. 14 shows the plurality of marker lines of FIG. 12 overlaid on the image of FIG. 9, with the acetabular cup impactor in a second position relative to the pelvic region.

Based on the received orientation data, and with reference to FIGS. 13 and 14, the processor 240 is adapted to overlay one or more second markers, more particularly alignment lines 271a-e, in images 270a, 270b displayed by the display device 220 such that, when the ASIS vector line 140, as seen in the images, is substantially aligned with one or more of the alignment lines 271a-271e, the acetabular cup impactor 10 will be oriented at the desired angle of inclination.

In order to provide this guidance for the inclination angle, the processor 240 is adapted to determine the appropriate orientation for the plurality of alignment lines 271a-e, when overlaid at respective positions in the images 270. The appropriate orientation of the alignment lines 271a-e, when overlaid in the images, is partially dependent on the position in the images at which they are to be overlaid, due to the angular range of the field of view of the camera. This means that the orientations of items as seen within images, such as the ASIS vector line 140, are dependent not only on their actual orientation relative to the impactor 10, but on where in the field of view of the camera those items are positioned.

Figure 11:
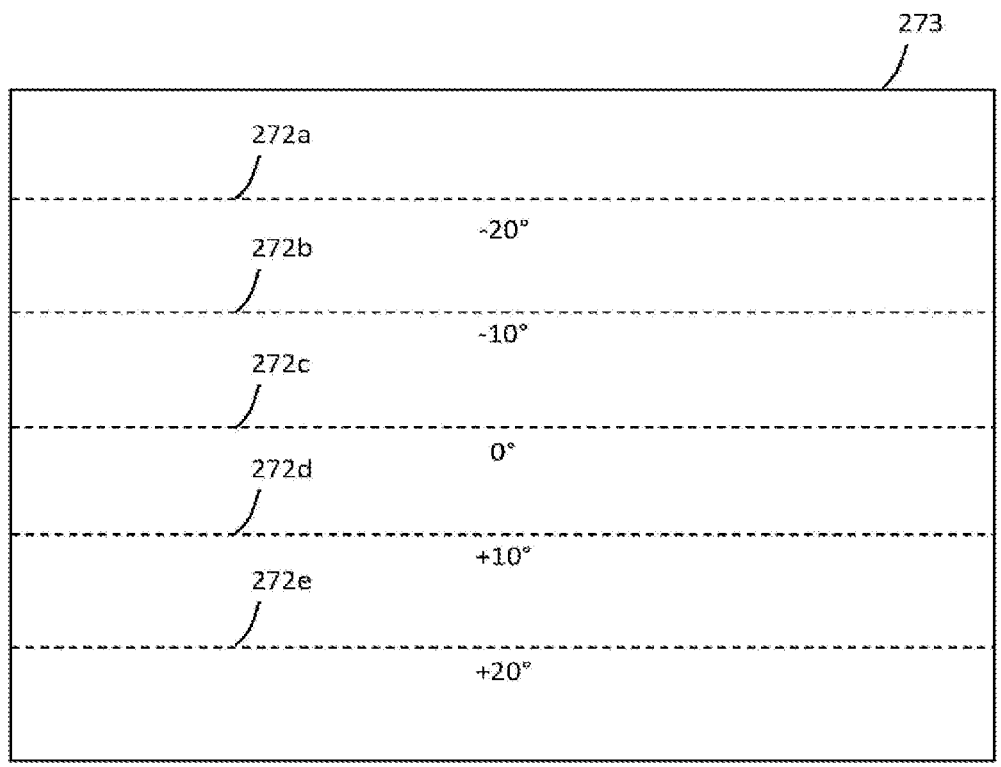
FIG. 11 shows an outline of the area covered by the image of FIG. 9, with guidelines positioned at different locations in the area, the guidelines being indicative of positions in the area that corresponding to 10° intervals within the field of view of the camera.

In this embodiment, the processor 240 is adapted to overlay five alignment lines 271a-e in the images 270a, 270b in accordance with equally spaced angular distances along the vertical axis of the field of view of the camera 210. In this embodiment, the camera 210 has a field of view of about 50° to 60° and the alignment lines are located, and their orientation determined, with respect to angular distances in the vertical axis of −20°, −10°, 0°, +10° and +20°, from the central horizontal axis of the camera's field of view. These angular distances are represented by guidelines 272a-e in FIG. 11, where FIG. 11 shows an outline 273 of the area covered by the image 270 of FIG. 9.

Using Equation 1, the processor 240 is adapted to determine for each angular distance (d) from the central horizontal line within the field of view of the camera, and for a measured anteversion angle (x) and a desired inclination angle (y), the angle (g) at which to orient alignment lines 271a-e that are to be overlaid in the images presented on the display.

$$\tan g = \tan(y) \cdot \sin(x+d) \qquad \text{Equation 1}$$

Figure 12:
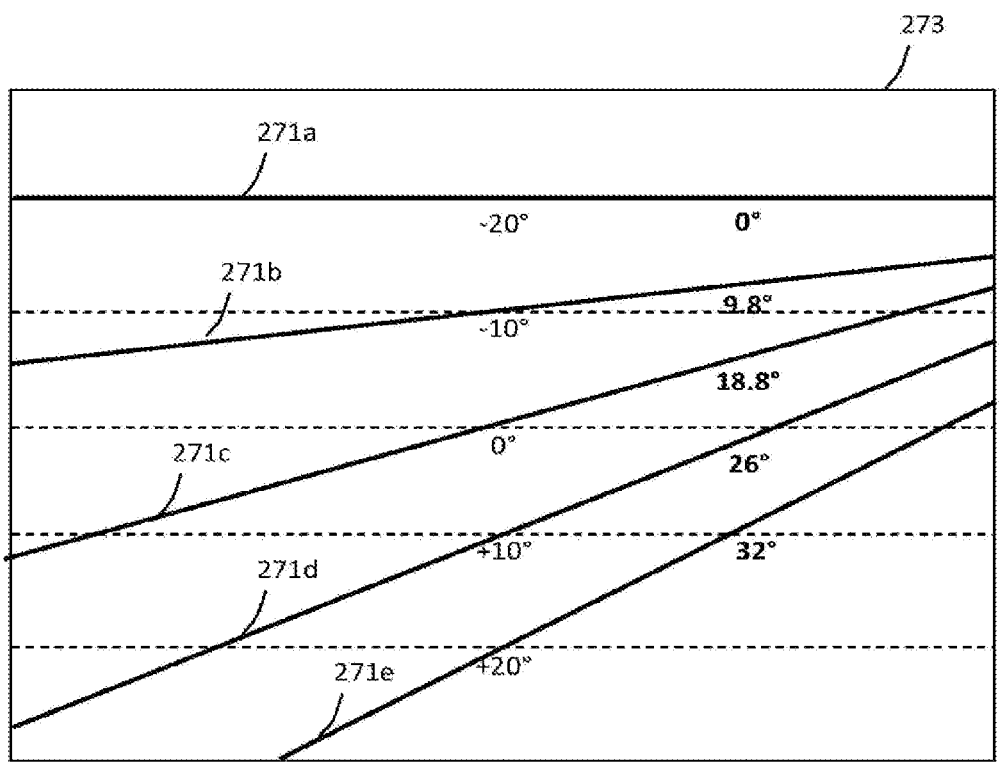
FIG. 12 shows a plurality of marker lines, each positioned with reference to one of the guidelines of FIG. 11, the marker lines being for guiding positioning of an acetabular cup impactor of the apparatus of FIG. 8.

Example orientations for the alignment lines 271a-e as determined using Equation 1 for each of the angular distances (d) are represented in FIG. 12, each alignment line 271a-e being overlaid next to a respective guideline 272a-272e. The orientations angles (g) can continually change as a result of the measured anteversion angle (x) changing as indicated above, and thus the alignment lines 271a-e can be seen to rotate within the screen as the impactor 1 is moved.

FIG. 13 shows a first image 270a as seen on the display by the surgeon, when the alignment lines 271a-271e have been overlaid by the processor 240. In the corner of the image 270a, the measured anteversion angle 274 is presented and continually updated as the impactor 10 moves.

The desired angle of inclination of the impactor 10 is achieved when the ASIS vector line 140 is substantially aligned with the nearest alignment line or lines 271a-e. In FIG. 13, the vector line 140 can be seen in image 270a positioned nearest the top two alignment lines 271a, 271b. The vector line 140 is substantially misaligned with these alignment lines 271a, 271b. This indicates that the impactor 10 is not at the desired angle of inclination. Furthermore, the anteversion angle 274 as presented on the display is at 23°, rather than a desired angle of 20°.

However, through movement of the impactor 10, and observation of the display 220, the surgeon can move the impactor 10 to a position as represented in the image 270b of FIG. 14. In this image 270b, the vector line 140 is substantially aligned (i.e. substantially parallel) with the nearest alignment lines 271a, 271b and the anteversion angle 274 as presented on the display is at the desired angle of 20°. At this point, the desired orientation of the impactor 10, and thus the acetabular cup 110 connected to the impactor 10, is achieved.

As indicated, in this embodiment, the patient is in a supine position. However, the approach described above can be carried out, mutatis mutandis, with a patient in the lateral recumbent position. In this variation, the tilt sensor will provide the angle of inclination of the impactor, and the alignment lines will be used instead to arrive at the desired angle of anteversion. More particularly, when the ASIS vector line, as seen in the images, is substantially aligned with one or more of the alignment lines, the acetabular cup impactor will be oriented at the desired angle of anteversion.

Equation 2 can be utilised in place of Equation 1. In particular using Equation 2, the processor is adapted to determine for each angular distance (d) from a central horizontal line within the field of view of the camera, and for a measured inclination angle (y) and a desired anteversion angle (x), the angle (g) at which to orient alignment lines that are to be overlaid in the images presented on the display.

$$\tan g = \tan(x) \cdot \sin(y+d) \qquad \text{Equation 2}$$

Figure 15:
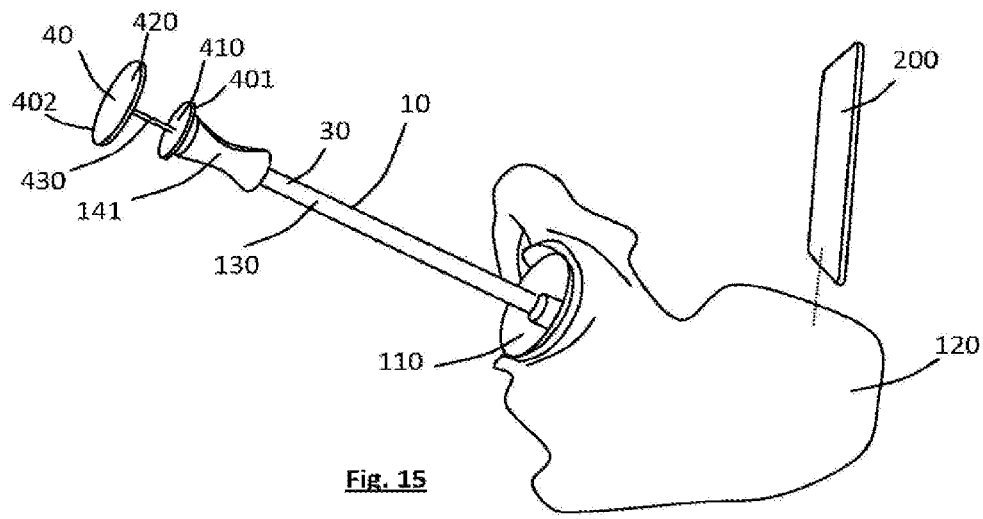
FIG. 15 shows apparatus according to another embodiment of the present disclosure.
Figure 17:
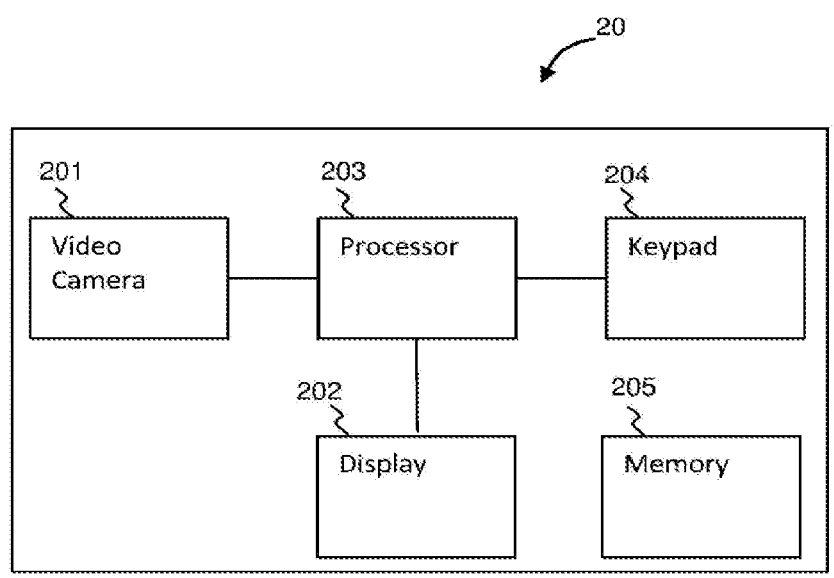
FIG. 17 shows a schematic view of elements of an electronic device used in the apparatus of FIG. 15.

FIG. 15 shows apparatus according to another embodiment of the present disclosure. The apparatus includes an acetabular cup impactor 10, adapted to drive and implant an acetabular cup 110 into position at the acetabulum of a patient's pelvic bone 120, and an electronic device 200, the electronic device 200 being mounted to the pelvic region, e.g. on the pelvic bone 120. With reference also to FIG. 17, the electronic device 200 includes an image capture device in the form of a video camera 201, a digital display 202, a processor 203, a touch keypad 204 and a memory 205 for data storage and retrieval. A tilt sensor may also be included. In this embodiment, the electronic device 200 is a tablet, e.g. an iPad™ although a variety of different electronic devices may be used. The camera 201, display 202, and processor 203 need not be integrated into a single device 200, nor all mounted on the pelvic region. For example, in one embodiment, the display and/or processor may be located remotely from the pelvic region.

The electronic device 200 is releasably fixed to the pelvic bone 120 or pelvic region via a mount (not shown) such that the camera 201 of the electronic device 200 faces the impactor 10. The electronic device 200 may be encased in a plastic covering. The plastic covering may hermetically seal the electronic device 200.

The camera 201 of the electronic device 200 is adapted to sequentially capture a plurality of images of the impactor 10 and the images are presented substantially in 'real time' on the display 202.

Figure 16:
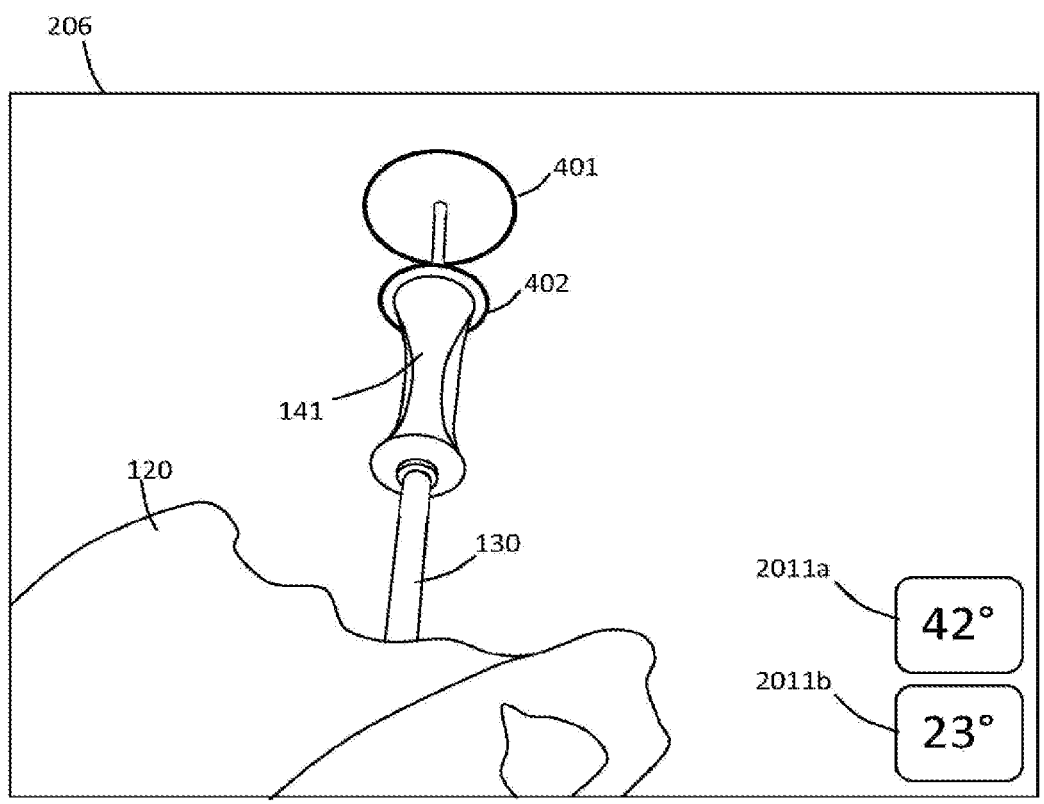
FIG. 16 shows an image of an acetabular cup impactor captured by a camera of the apparatus of FIG. 15.

A navigation element 40 in the form of two circular disks 410, 420, connected together by a spacer 430, is releasably mounted to the distal end of the impactor 10. The two disks 410, 420 are concentric and the centres of the disks 410, 420 are aligned with the longitudinal axis of the impactor 10. The disk 410 closest to the impactor 10 has a smaller diameter than the disk 420 furthest from the impactor 10. The edges 401, 402 of the disks define circles that provide two first markers. With reference to FIG. 16, which shows an example image (frame) 206 as presented on the display 202, the two first markers 401, 402 are visible in the image 206.

The processor 203 of the electronic device 200 is adapted to receive orientation data related to the impactor 10 (and the acetabular cup 110). In this embodiment, the patient is located in a supine position, and the orientation data received by the processor includes a desired inclination angle and a desired anteversion angle for the impactor. The desired inclination and anteversion angles, which are 45° and 20°, respectively, in this example, are input into the electronic device 200 using the touchscreen keypad 204.

Figure 18A:
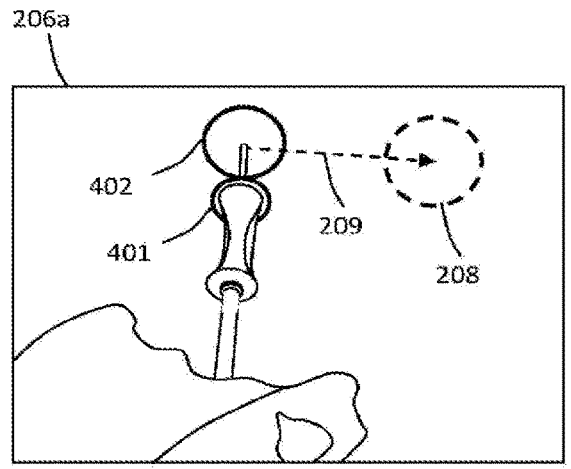
FIGS. 18a to 18d show calibration markers overlaid on images captured by the camera of the apparatus of FIG. 15.
Figure 18B:
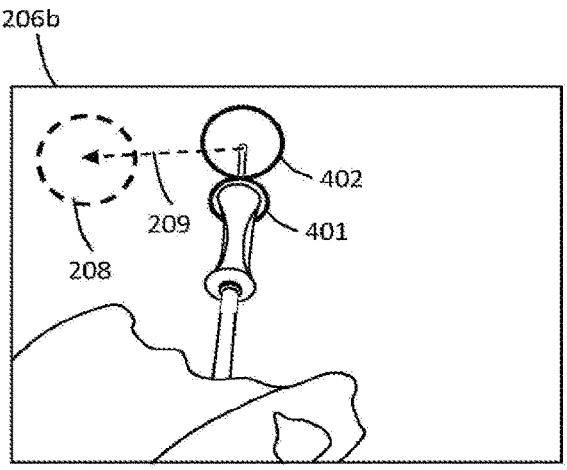
Figure 18C:
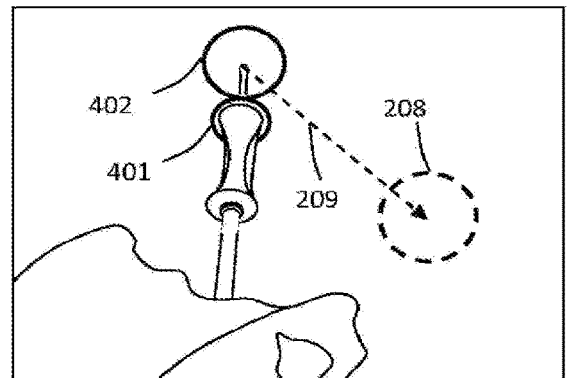
Figure 18D:
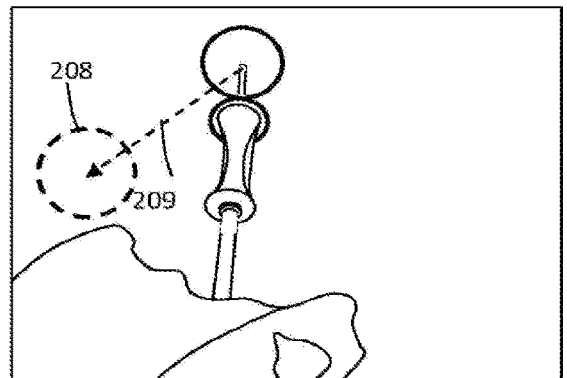

In this embodiment, a calibration procedure is performed to determine the pivot point of the impactor 10 relative to the camera 201 and the positions of the first markers along the longitudinal axis of the impactor 10. With reference to FIG. 18a, during the calibration procedure the processor 203 is adapted to overlay a third marker 208 in a first position in images 206a displayed by the display device 202. The impactor 10 is then moved by a surgeon, generally in a direction as indicated by arrow 209, such that one of the disks, in particular the larger disk 402 in this embodiment, is aligned with the third marker 208. Once aligned, the user is required to touch the screen, or 'click' a cursor on the screen, at the position in the image at which the other of the disks, in particular the smaller disk 401 in this embodiment, is located. This process is repeated for a number of different positions (e.g. second to fourth positions) of the third marker 209, as represented in images 206b-206d of FIGS. 18b to 18d. This enables a determination to be made of the exact and relative positions of the two first markers 401, 402 in the images 206a-206d, and through application of trigonometric functions, calibration data including the pivot position of the impactor relative to the camera, and the positions of the first markers along the longitudinal axis of the impactor, can also be determined.

Figure 19:
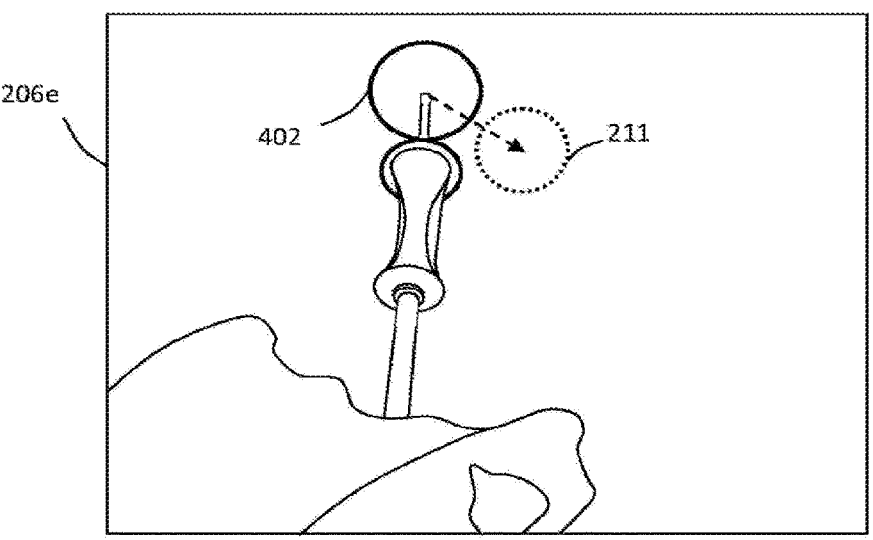
FIG. 19 shows an alignment marker overlaid on an image captured by the camera of the apparatus of FIG. 15.

Based on the calibration data and the received orientation data (i.e. the desired inclination and anteversion angles), the processor 203 is adapted to determine where in the displayed images a second marker 211 should be located to guide the impactor so that it has the desired inclination and anteversion angles. In this embodiment, with reference to FIG. 19, the processor 203 is adapted to overlay the second marker 211 in the images 206e displayed by the display device 202 such that, when the larger disk 402, as seen in the images, is substantially aligned with the second marker 211, the acetabular cup impactor 10 will be oriented at the desired orientation.

In a variation of this embodiment, the processor is adapted to use feature detection to determine the positions and shapes of the first markers 401, 402 within the images 206. The feature detection may be used in place of a user being required to touch or 'click' on the position of one of the first markers 401, in order to identify the position of that marker. Alternatively, feature detection may be used to remove the need for the calibration procedure entirely.

In more detail, to the extent that the centre of the camera 201 is misaligned with the longitudinal axis of the impactor 10, the first markers 401, 402 will appear as ellipses in the images 206. The shape (e.g. minor to major axis ratio) and relative positioning of the ellipses is dependent on the angle at which the impactor 10 is located. Following from this, feature detection can be used to determine the inclination and anteversion angles for the impactor 10, and these angles can be presented by the processor 203 substantially in 'real time' on the images 206, e.g., within boxes 2011a, 2011b in the image 206 as shown in FIG. 16. This enables a surgeon to move the impactor 10 to the desired orientation based on observation of changes to the displayed angles. Alternatively or additionally, based on the feature detection and user input of the desired inclination and anteversion angles, a second marker can be overlaid on the images to guide movement of the impactor 10 to the desired orientation.

Figure 20:
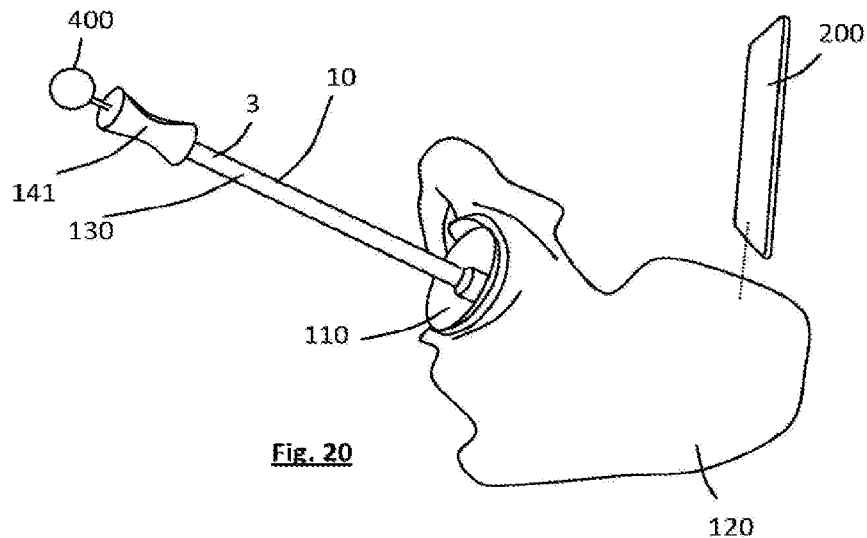
FIG. 20 shows apparatus according to another embodiment of the present disclosure.
Figure 21:
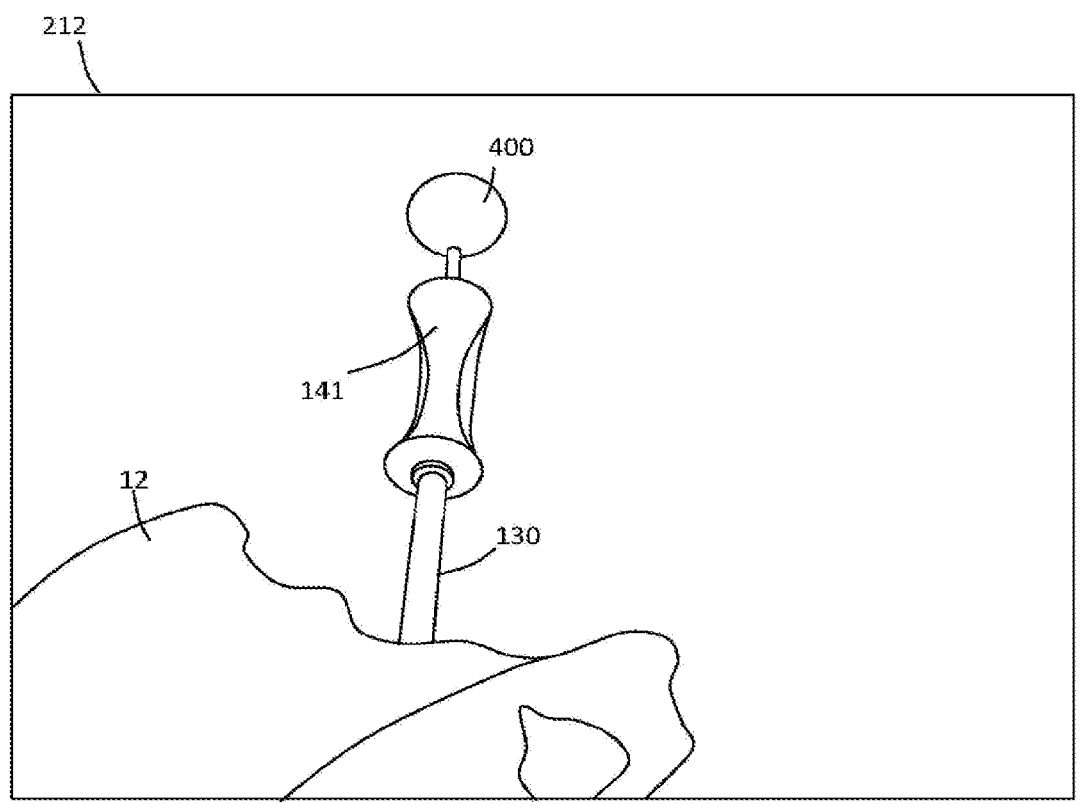
FIG. 21 shows an image of an acetabular cup impactor captured by a camera of the apparatus of FIG. 20.

With reference to FIG. 20, in an alternative embodiment, apparatus is provided that is substantially identical to the apparatus shown in FIG. 15, but which employs a different type of navigation element, in particular a navigation element in the form of a sphere 400 that is releasably mounted at the distal end of the impactor 10. The sphere 400 provides a first marker. With reference to FIG. 21, which shows an example image (frame) 212 as presented on the display, the first marker 400 is visible in the image 212.

Figure 22A:
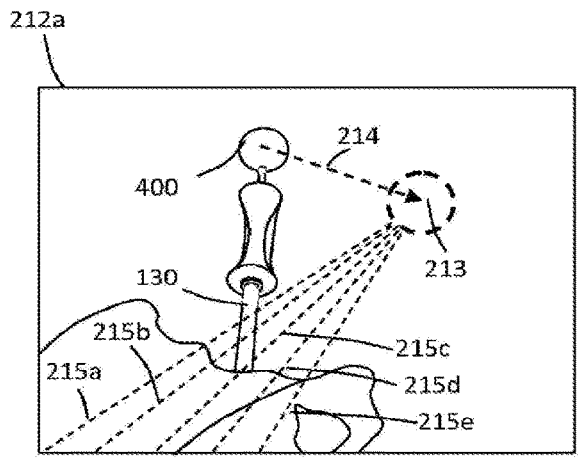
FIGS. 22a to 22d show calibration markers overlaid on images captured by the camera of the apparatus of FIG. 20.
Figure 22B:
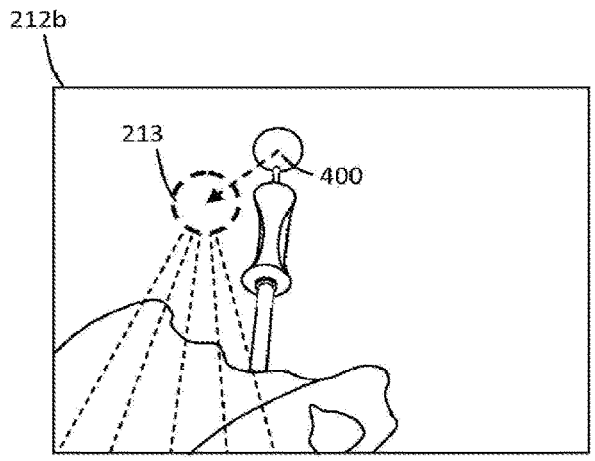
Figure 22C:
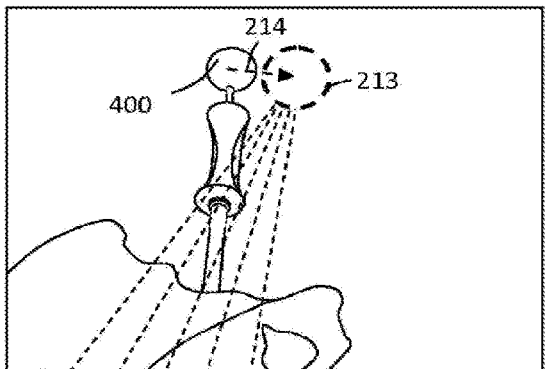
Figure 22D:
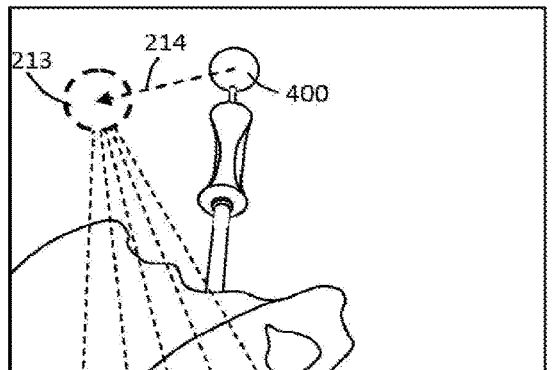

Again, in this embodiment, a calibration procedure is performed to determine the pivot point of the impactor relative to the camera 201, and the positions of the first marker 400 along the longitudinal axis of the impactor 10. With reference to FIG. 22a, during the calibration procedure the processor 203 is adapted to overlay a third marker 213 in a first position in images 212a displayed by the display device. The impactor 10 is then moved by the surgeon, generally as indicated by arrow 214, such that the first marker 400 is aligned with the third marker 213. Once aligned, the user is required to touch the screen, or 'click', at one of a plurality of guidelines 215a-215e that are overlaid on the screen, which guideline 215a-215e has the closest angular relationship to the angle of extension of the shaft 130 as seen within the image 212a. This process is repeated for a number of different positions (e.g. second to fourth positions) of the third marker 213, as represented in images 212b-212d of FIGS. 22b to 22d. This enables a determination to be made of the positioning of the first marker 400 and the angle of extension of the shaft 130 of the impactor 10 within the images, and through application of trigonometric functions, calibration data including the pivot position of the impactor relative to the camera, and the positions of the first marker along the longitudinal axis of the impactor, can also be determined.

Figure 23:
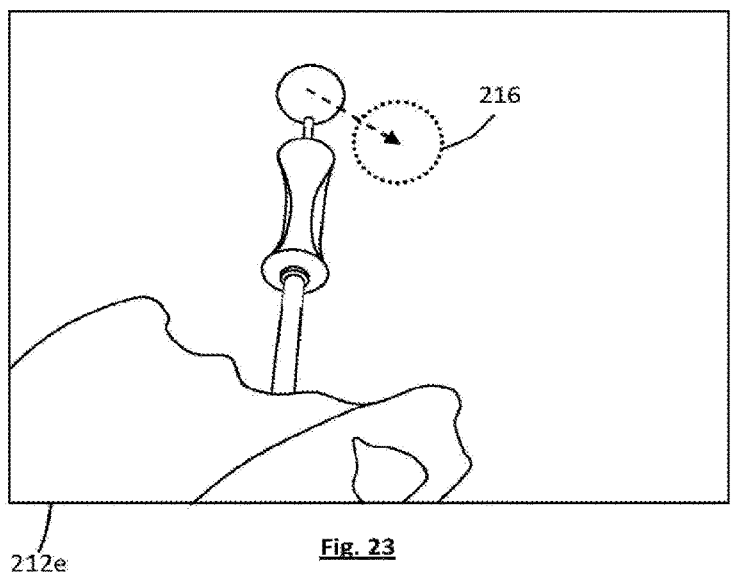
FIG. 23 shows an alignment marker overlaid on an image captured by the camera of the apparatus of FIG. 20.

Based on the calibration data and the received orientation data (i.e. the desired inclination and anteversion angles), the processor 203 is adapted to determine where in images a second marker 216 should be located to guide the impactor 10 so that it has the desired inclination and anteversion angles. In this embodiment, with reference to FIG. 23, the processor 203 is adapted to overlay the second marker 216 in the images 212e displayed by the display device 22 such that, when the sphere 400, as seen in the images, is substantially aligned with the second marker 216, the acetabular cup impactor 10 will be oriented at the desired orientation.

While the use of navigation elements, feature detection, and calibration steps, etc., is described in conjunction with FIGS. 15 to 23, where the image capture device is mounted to the pelvic region, substantially the same navigation elements, feature detection, and calibration steps, etc., may be employed, mutatis mutandis, when the image capture device is mounted on the impactor 10, e.g. as shown in FIG. 8. In this variation, navigation elements similar to those described in FIGS. 15 to 23 may be mounted on the pelvic region, for example.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of determining an orientation of an acetabular cup impactor, comprising:
   recording a reference orientation of a patient's pelvic region using an electronic orientation sensor located at a first location on the patient's pelvic region, wherein in the first location the electronic orientation sensor is not coupled with a mechanical device while the mechanical device is engaged within an acetabulum of the patient, and
   monitoring an orientation of an acetabular cup impactor relative to the reference orientation using the electronic orientation sensor when the electronic orientation sensor is located at a second location on the acetabular cup impactor after being transitioned to the second location from the first location, the acetabular cup impactor being moveable to a desired orientation relative to the patient's pelvic region for implantation of an acetabular cup into the acetabulum.

2. The method of claim 1, further comprising engaging the orientation sensor and the pelvic region with a first mount to releasably fix the positions of the orientation sensor and the pelvic region relative to each other when the orientation sensor is located at the first location.

3. The method of claim 1, further comprising engaging the orientation sensor and the impactor with a second mount to releasably fix the positions of the orientation sensor and the impactor relative to each other when the orientation sensor is located at the second location.

4. The method of claim 1, wherein monitoring the orientation of the acetabular cup impactor relative to the reference orientation comprises monitoring the orientation in three-dimensional space.

5. The method of claim 4, wherein monitoring the orientation of the acetabular cup impactor relative to the reference orientation comprises monitoring an angle of anteversion and an angle inclination of the acetabular cup impactor.

6. The method of claim 1, further comprising providing the monitored orientation of the impactor or the recorded reference orientation to a clinician or other user.

7. The method of claim 6, wherein providing the monitored orientation of the impactor or the recorded reference orientation comprises displaying the orientation of the impactor or the recorded reference orientation on a display.

8. The method of claim 7, wherein the display is comprised in the electronic orientation sensor.

9. The method of claim 1, wherein the orientation sensor is comprised in a smartphone or a tablet computer.

10. The method of claim 1, wherein the monitored orientation or the reference orientation is determined using one or more of an accelerometer, a magnetic field sensor and a gyroscope comprised in the orientation sensor.

11. A non-transitory computer readable storage medium having stored thereon instruction which, when executed, cause a processor to perform a method comprising:
    recording a reference orientation of a patient's pelvic region using an electronic orientation sensor located at a first location on the patient's pelvic region, wherein in the first location the electronic orientation sensor is not coupled with a mechanical device while the mechanical device is engaged within an acetabulum of the patient, and
    monitoring an orientation of an acetabular cup impactor relative to the reference orientation using the electronic orientation sensor when the electronic orientation sensor is located at a second location on the acetabular cup impactor after being transitioned to the second location from the first location, the acetabular cup impactor being moveable to a desired orientation relative to the patient's pelvic region for implantation of an acetabular cup into the acetabulum.

* * * * *